United States Patent
Grote et al.

(10) Patent No.: US 7,435,883 B2
(45) Date of Patent: *Oct. 14, 2008

(54) INBRED CORN LINE PH8JR

(75) Inventors: Edwin Michael Grote, Milton, WI (US); Joseph Kevin Gogerty, Algona, IA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 44 days.

This patent is subject to a terminal disclaimer.

(21) Appl. No.: 11/173,619

(22) Filed: Jul. 1, 2005

(65) Prior Publication Data

US 2006/0010534 A1  Jan. 12, 2006

Related U.S. Application Data

(63) Continuation of application No. 10/769,189, filed on Jan. 30, 2004, now Pat. No. 6,967,269.

(51) Int. Cl.
*A01H 1/00* (2006.01)
*A01H 4/00* (2006.01)
*A01H 5/00* (2006.01)
*A01H 5/10* (2006.01)
*C12N 15/82* (2006.01)

(52) U.S. Cl. .................... 800/320.1; 435/412; 800/275; 800/278; 800/279; 800/281; 800/298; 800/300.1; 800/301; 800/302; 800/303

(58) Field of Classification Search ....................... None
See application file for complete search history.

(56) References Cited

U.S. PATENT DOCUMENTS 5,689,034 A  11/1997  Fullerton
6,130,370 A  10/2000  Benson et al.

OTHER PUBLICATIONS

Plant Variety Protection Certificate No. 200100247 for Corn PH7CP, issued May 23, 2003.
Plant Variety Protection Certificate No. 9900384 for Corn PH1B8, issued Nov. 6, 2001.
Plant Variety Protection Certificate No. 9600204 for Corn PH24E, issued Jul. 30, 1999.

*Primary Examiner*—David H Kruse
(74) *Attorney, Agent, or Firm*—McKee, Voorhees & Sease, P.L.C.

(57) ABSTRACT

A novel inbred maize line designated PH8JR and seed, plants and plant parts thereof. Methods for producing a maize plant that comprise crossing inbred maize line PH8JR with another maize plant. Methods for producing a maize plant containing in its genetic material one or more traits introgressed into PH8JR through backcross conversion and/or transformation, and to the maize seed, plant and plant part produced thereby. Hybrid maize seed, plant or plant part produced by crossing the inbred line PH8JR or an introgressed trait conversion of PH8JR with another maize line. Inbred maize lines derived from inbred maize line PH8JR, methods for producing other inbred maize lines derived from inbred maize line PH8JR and the inbred maize lines and their parts derived by the use of those methods.

32 Claims, No Drawings

INBRED CORN LINE PH8JR

This application is a continuation of application Ser. No. 10/769,189, now U.S. Pat. No. 6,967,269, filed Jan. 30, 2004. The instant application incorporates herein the disclosure of application Ser. No. 10/769,189, now U.S. Pat. No. 6,967,269, in its entirety, by reference.

FIELD OF THE INVENTION

This invention relates generally to the field of maize breeding, specifically relating to an inbred maize line designated PH8JR.

BACKGROUND OF THE INVENTION

The goal of plant breeding is to combine, in a single variety or hybrid, various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination, stand establishment, growth rate, maturity, plant height and ear height, is important. Traditional plant breeding is an important tool in developing new and improved commercial crops.

SUMMARY OF THE INVENTION

According to the invention, there is provided a novel inbred maize line, designated PH8JR and processes for making PH8JR. This invention relates to seed of inbred maize line PH8JR, to the plants of inbred maize line PH8JR, to plant parts of inbred maize line PH8JR, and to processes for making a maize plant that comprise crossing inbred maize line PH8JR with another maize plant. This invention also relates to processes for making a maize plant containing in its genetic material one or more traits introgressed into PH8JR through backcross conversion and/or transformation, and to the maize seed, plant and plant part produced by such introgression. This invention further relates to a hybrid maize seed, plant or plant part produced by crossing the inbred line PH8JR or an introgressed trait conversion of PH8JR with another maize line. This invention also relates to inbred maize lines derived from inbred maize line PH8JR, to processes for making other inbred maize lines derived from inbred maize line PH8JR and to the inbred maize lines and their parts derived by the use of those processes.

Definitions

Certain definitions used in the specification are provided below. Also in the examples that follow, a number of terms are used herein. In order to provide a clear and consistent understanding of the specification and claims, including the scope to be given such terms, the following definitions are provided. NOTE: ABS is in absolute terms and % MN is percent of the mean for the experiments in which the inbred or hybrid was grown. PCT designates that the trait is calculated as a percentage. % NOT designates the percentage of plants that did not exhibit a trait. For example, STKLDG % NOT is the percentage of plants in a plot that were not stalk lodged. These designators will follow the descriptors to denote how the values are to be interpreted.

ABTSTK=ARTIFICIAL BRITTLE STALK. A count of the number of "snapped" plants per plot following machine snapping. A snapped plant has its stalk completely snapped at a node between the base of the plant and the node above the ear. Expressed as percent of plants that did not snap.

ALLELE. Any of one or more alternative forms of a genetic sequence. Typically, in a diploid cell or organism, the two alleles of a given sequence typically occupy corresponding loci on a pair of homologous chromosomes.

ANT ROT=ANTHRACNOSE STALK ROT (*Colletotrichum graminicola*). A 1 to 9 visual rating indicating the resistance to Anthracnose Stalk Rot. A higher score indicates a higher resistance.

BACKCROSSING. Process in which a breeder crosses a hybrid progeny line back to one of the parental genotypes one or more times.

BARPLT=BARREN PLANTS. The percent of plants per plot that were not barren (lack ears).

BREEDING. The genetic manipulation of living organisms.

BREEDING CROSS. A cross to introduce new genetic material into a plant for the development of a new variety. For example, one could cross plant A with plant B, wherein plant B would be genetically different from plant A. After the breeding cross, the resulting F1 plants could then be selfed or sibbed for one, two, three or more times (F1, F2, F3, etc.) until a new inbred variety is developed. For clarification, such new inbred varieties would be within a pedigree distance of one breeding cross of plants A and B. The process described above would be referred to as one breeding cycle.

BRTSTK=BRITTLE STALKS. This is a measure of the stalk breakage near the time of pollination, and is an indication of whether a hybrid or inbred would snap or break near the time of flowering under severe winds. Data are presented as percentage of plants that did not snap.

CELL. Cell as used herein includes a plant cell, whether isolated, in tissue culture or incorporated in a plant or plant part.

CLDTST=COLD TEST. The percent of plants that germinate under cold test conditions.

CLN=CORN LETHAL NECROSIS. Synergistic interaction of maize chlorotic mottle virus (MCMV) in combination with either maize dwarf mosaic virus (MDMV-A or MDMV-B) or wheat streak mosaic virus (WSMV). A 1 to 9 visual rating indicating the resistance to Corn Lethal Necrosis. A higher score indicates a higher resistance.

COMRST=COMMON RUST (*Puccinia sorghi*). A 1 to 9 visual rating indicating the resistance to Common Rust. A higher score indicates a higher resistance.

CROSS POLLINATION. A plant is cross pollinated if the pollen comes from a flower on a different plant from a different family or line. Cross pollination excludes sib and self pollination.

CROSS. As used herein, the term "cross" or "crossing" can refer to a simple X by Y cross, or the process of backcrossing, depending on the context.

D/D=DRYDOWN. This represents the relative rate at which a hybrid will reach acceptable harvest moisture compared to other hybrids on a 1 to 9 rating scale. A high score indicates a hybrid that dries relatively fast while a low score indicates a hybrid that dries slowly.

DIPERS=DIPLODIA EAR MOLD SCORES (*Diplodia maydis* and *Diplodia macrospora*). A 1 to 9 visual rating indicating the resistance to Diplodia Ear Mold. A higher score indicates a higher resistance.

DIPLOID PLANT PART. Refers to a plant part or cell that has the same diploid genotype as PH8JR.

DIPROT=DIPLODIA STALK ROT SCORE. Score of stalk rot severity due to Diplodia (*Diplodia maydis*). Expressed as a 1 to 9 score with 9 being highly resistant.

DRPEAR=DROPPED EARS. A measure of the number of dropped ears per plot and represents the percentage of plants that did not drop ears prior to harvest.

D/T=DROUGHT TOLERANCE. This represents a 1 to 9 rating for drought tolerance, and is based on data obtained under stress conditions. A high score indicates good drought tolerance and a low score indicates poor drought tolerance.

EARHT=EAR HEIGHT. The ear height is a measure from the ground to the highest placed developed ear node attachment and is measured in centimeters.

EARMLD=GENERAL EAR MOLD. Visual rating (1 to 9 score) where a "1" is very susceptible and a "9" is very resistant. This is based on overall rating for ear mold of mature ears without determining the specific mold organism, and may not be predictive for a specific ear mold.

EARSZ=EAR SIZE. A 1 to 9 visual rating of ear size. The higher the rating the larger the ear size.

EBTSTK=EARLY BRITTLE STALK. A count of the number of "snapped" plants per plot following severe winds when the corn plant is experiencing very rapid vegetative growth in the V5-V8 stage. Expressed as percent of plants that did not snap.

ECB1LF=EUROPEAN CORN BORER FIRST GENERATION LEAF FEEDING (*Ostrinia nubilalis*). A 1 to 9 visual rating indicating the resistance to preflowering leaf feeding by first generation European Corn Borer. A higher score indicates a higher resistance.

ECB21T=EUROPEAN CORN BORER SECOND GENERATION INCHES OF TUNNELING (*Ostrinia nubilalis*). Average inches of tunneling per plant in the stalk.

ECB2SC=EUROPEAN CORN BORER SECOND GENERATION (*Ostrinia nubilalis*). A 1 to 9 visual rating indicating post flowering degree of stalk breakage and other evidence of feeding by European Corn Borer, Second Generation. A higher score indicates a higher resistance.

ECBDPE=EUROPEAN CORN BORER DROPPED EARS (*Ostrinia nubilalis*). Dropped ears due to European Corn Borer. Percentage of plants that did not drop ears under second generation corn borer infestation.

EGRWTH=EARLY GROWTH. This is a measure of the relative height and size of a corn seedling at the 2-4 leaf stage of growth. This is a visual rating (1 to 9), with 1 being weak or slow growth, 5 being average growth and 9 being strong growth. Taller plants, wider leaves, more green mass and darker color constitute higher score.

ELITE INBRED. An inbred that contributed desirable qualities when used to produce commercial hybrids. An elite inbred may also be used in further breeding for the purpose of developing further improved varieties.

ERTLDG=EARLY ROOT LODGING. Early root lodging is the percentage of plants that do not root lodge prior to or around anthesis; plants that lean from the vertical axis at an approximately 30 degree angle or greater would be counted as root lodged.

ERTLPN=EARLY ROOT LODGING. An estimate of the percentage of plants that do not root lodge prior to or around anthesis; plants that lean from the vertical axis at an approximately 30 degree angle or greater would be considered as root lodged.

ERTLSC=EARLY ROOT LODGING SCORE. Score for severity of plants that lean from a vertical axis at an approximate 30 degree angle or greater which typically results from strong winds prior to or around flowering recorded within 2 weeks of a wind event. Expressed as a 1 to 9 score with 9 being no lodging.

ESTCNT=EARLY STAND COUNT. This is a measure of the stand establishment in the spring and represents the number of plants that emerge on per plot basis for the inbred or hybrid.

EYESPT=EYE SPOT (*Kabatiella zeae* or *Aureobasidium zeae*). A 1 to 9 visual rating indicating the resistance to Eye Spot. A higher score indicates a higher resistance.

FUSERS=FUSARIUM EAR ROT SCORE (*Fusarium moniliforme* or *Fusarium subglutinans*). A 1 to 9 visual rating indicating the resistance to Fusarium ear rot. A higher score indicates a higher resistance.

GDU=GROWING DEGREE UNITS. Using the Barger Heat Unit Theory, which assumes that maize growth occurs in the temperature range 50 degrees F.-86 degrees F. and that temperatures outside this range slow down growth; the maximum daily heat unit accumulation is 36 and the minimum daily heat unit accumulation is 0. The seasonal accumulation of GDU is a major factor in determining maturity zones.

GDUSHD=GDU TO SHED. The number of growing degree units (GDUs) or heat units required for an inbred line or hybrid to have approximately 50 percent of the plants shedding pollen and is measured from the time of planting. Growing degree units are calculated by the Barger Method, where the heat units for a 24-hour period are:

$$GDU = \frac{(\text{Max. temp.} + \text{Min. temp.})}{2} - 50$$

The highest maximum temperature used is 86 degrees F. and the lowest minimum temperature used is 50 degrees F. For each inbred or hybrid it takes a certain number of GDUs to reach various stages of plant development.

GDUSLK=GDU TO SILK. The number of growing degree units required for an inbred line or hybrid to have approximately 50 percent of the plants with silk emergence from time of planting. Growing degree units are calculated by the Barger Method as given in GDU SHD definition.

GENOTYPE. Refers to the genetic constitution of a cell or organism.

GIBERS=GIBBERELLA EAR ROT (PINK MOLD) (*Gibberella zeae*). A 1 to 9 visual rating indicating the resistance to *Gibberella* Ear Rot. A higher score indicates a higher resistance.

GIBROT=GIBBERELLA STALK ROT SCORE. Score of stalk rot severity due to *Gibberella* (*Gibberella zeae*). Expressed as a 1 to 9 score with 9 being highly resistant.

GLFSPT=GRAY LEAF SPOT (*Cercospora zeae-maydis*). A 1 to 9 visual rating indicating the resistance to Gray Leaf Spot. A higher score indicates a higher resistance.

GOSWLT=GOSS' WILT (*Corynebacterium nebraskense*). A 1 to 9 visual rating indicating the resistance to Goss' Wilt. A higher score indicates a higher resistance.

GRNAPP=GRAIN APPEARANCE. This is a 1 to 9 rating for the general appearance of the shelled grain as it is harvested based on such factors as the color of harvested grain, any mold on the grain, and any cracked grain. High scores indicate good grain visual quality.

HAPLOID PLANT PART. Refers to a plant part or cell that has the same haploid genotype as PH8JR.

HCBLT=HELMINTHOSPORIUM CARBONUM LEAF BLIGHT (*Helminthosporium carbonum*). A 1 to 9 visual rating indicating the resistance to *Helminthosporium* infection. A higher score indicates a higher resistance.

HD SMT=HEAD SMUT (*Sphacelotheca reiliana*). This score indicates the percentage of plants not infected.

HSKCVR=HUSK COVER. A 1 to 9 score based on performance relative to key checks, with a score of 1 indicating very short husks, tip of ear and kernels showing; 5 is intermediate coverage of the ear under most conditions, sometimes with thin husk; and a 9 has husks extending and closed beyond the tip of the ear. Scoring can best be done near physiological maturity stage or any time during dry down until harvested.

INC D/A=GROSS INCOME (DOLLARS PER ACRE). Relative income per acre assuming drying costs of two cents per point above 15.5 percent harvest moisture and current market price per bushel.

INCOME/ACRE. Income advantage of hybrid to be patented over other hybrid on per acre basis.

INC ADV=GROSS INCOME ADVANTAGE. GROSS INCOME advantage of variety #1 over variety #2.

KSZDCD=KERNEL SIZE DISCARD. The percent of discard seed; calculated as the sum of discarded tip kernels and extra large kernels.

LINKAGE. Refers to a phenomenon wherein alleles on the same chromosome tend to segregate together more often than expected by chance if their transmission was independent.

LINKAGE DISEQUILIBRIUM. Refers to a phenomenon wherein alleles tend to remain together in linkage groups when segregating from parents to offspring, with a greater frequency than expected from their individual frequencies.

L/POP=YIELD AT LOW DENSITY. Yield ability at relatively low plant densities on a 1 to 9 relative system with a higher number indicating the hybrid responds well to low plant densities for yield relative to other hybrids. A 1, 5, and 9 would represent very poor, average, and very good yield response, respectively, to low plant density.

LRTLDG=LATE ROOT LODGING. Late root lodging is the percentage of plants that do not root lodge after anthesis through harvest; plants that lean from the vertical axis at an approximately 30 degree angle or greater would be counted as root lodged.

LRTLPN=LATE ROOT LODGING. Late root lodging is an estimate of the percentage of plants that do not root lodge after anthesis through harvest; plants that lean from the vertical axis at an approximately 30 degree angle or greater would be considered as root lodged.

LRTLSC=LATE ROOT LODGING SCORE. Score for severity of plants that lean from a vertical axis at an approximate 30 degree angle or greater which typically results from strong winds after flowering. Recorded prior to harvest when a root-lodging event has occurred. This lodging results in plants that are leaned or "lodged" over at the base of the plant and do not straighten or "goose-neck" back to a vertical position. Expressed as a 1 to 9 score with 9 being no lodging.

MDMCPX=MAIZE DWARF MOSAIC COMPLEX (MDMV=Maize Dwarf Mosaic Virus and MCDV=Maize Chlorotic Dwarf Virus). A 1 to 9 visual rating indicating the resistance to Maize Dwarf Mosaic Complex. A higher score indicates a higher resistance.

MST=HARVEST MOISTURE. The moisture is the actual percentage moisture of the grain at harvest.

MSTADV=MOISTURE ADVANTAGE. The moisture advantage of variety #1 over variety #2 as calculated by: MOISTURE of variety #2—MOISTURE of variety #1=MOISTURE ADVANTAGE of variety #1.

NLFBLT=NORTHERN LEAF BLIGHT (*Helminthosporium turcicum* or *Exserohilum turcicum*). A 1 to 9 visual rating indicating the resistance to Northern Leaf Blight. A higher score indicates a higher resistance.

OILT=GRAIN OIL. Absolute value of oil content of the kernel as predicted by Near-infrared Transmittance and expressed as a percent of dry matter.

PEDIGREE DISTANCE. Relationship among generations based on their ancestral links as evidenced in pedigrees. May be measured by the distance of the pedigree from a given starting point in the ancestry.

PERCENT IDENTITY. Percent identity as used herein refers to the comparison of the homozygous alleles of two inbred lines. Each inbred plant will have the same allele (and therefore be homozygous) at almost all of their loci. Percent identity is determined by comparing a statistically significant number of the homozygous alleles of two inbred lines. For example, a percent identity of 90% between inbred PH8JR and other inbred line means that the two inbred lines have the same allele at 90% of their loci.

PERCENT SIMILARITY. Percent similarity as used herein refers to the comparison of the homozygous alleles of an inbred line with another plant. The homozygous alleles of PH8JR are compared with the alleles of a non-inbred plant, such as a hybrid, and if the allele of the inbred matches at least one of the alleles from the hybrid then they are scored as similar. Percent similarity is determined by comparing a statistically significant number of loci and recording the number of loci with similar alleles as a percentage. For example, a percent similarity of 90% between inbred PH8JR and a hybrid maize plant means that the inbred line matches at least one of the hybrid alleles at 90% of the loci. In the case of a hybrid produced from PH8JR as the male or female parent, such hybrid will comprise two sets of alleles, one set of which will comprise the same alleles as the homozygous alleles of inbred line PH8JR.

PLANT. As used herein, the term "plant" includes reference to an immature or mature whole plant, including a plant that has been detasseled or from which seed or grain has been removed. Seed or embryo that will produce the plant is also considered to be the plant.

PLANT PARTS. As used herein, the term "plant parts" includes leaves, stems, roots, seed, grain, embryo, pollen, ovules, flowers, ears, cobs, husks, stalks, root tips, anthers, pericarp, silk, tissue, cells and the like.

PLTHT=PLANT HEIGHT. This is a measure of the height of the plant from the ground to the tip of the tassel in centimeters.

POLSC=POLLEN SCORE. A 1 to 9 visual rating indicating the amount of pollen shed. The higher the score the more pollen shed.

POLWT=POLLEN WEIGHT. This is calculated by dry weight of tassels collected as shedding commences minus dry weight from similar tassels harvested after shedding is complete.

POP KIA=PLANT POPULATIONS. Measured as 1000s per acre.

POP ADV=PLANT POPULATION ADVANTAGE. The plant population advantage of variety #1 over variety #2 as calculated by PLANT POPULATION of variety #2—PLANT POPULATION of variety #1=PLANT POPULATION ADVANTAGE of variety #1.

PRM=PREDICTED RELATIVE MATURITY. This trait, predicted relative maturity, is based on the harvest moisture of the grain. The relative maturity rating is based on a known set of checks and utilizes standard linear regression analyses and is also referred to as the Comparative Relative Maturity Rating System that is similar to the Minnesota Relative Maturity Rating System.

PRMSHD=A relative measure of the growing degree units (GDU) required to reach 50% pollen shed. Relative values are predicted values from the linear regression of observed GDU's on relative maturity of commercial checks.

PROT=GRAIN PROTEIN. Absolute value of protein content of the kernel as predicted by Near-Infrared Transmittance and expressed as a percent of dry matter.

RTLDG=ROOT LODGING. Root lodging is the percentage of plants that do not root lodge; plants that lean from the vertical axis at an approximately 30 degree angle or greater would be counted as root lodged.

RTLADV=ROOT LODGING ADVANTAGE. The root lodging advantage of variety #1 over variety #2.

SCTGRN=SCATTER GRAIN. A 1 to 9 visual rating indicating the amount of scatter grain (lack of pollination or kernel abortion) on the ear. The higher the score the less scatter grain.

SDGVGR=SEEDLING VIGOR. This is the visual rating (1 to 9) of the amount of vegetative growth after emergence at the seedling stage (approximately five leaves). A higher score indicates better vigor.

SEL IND=SELECTION INDEX. The selection index gives a single measure of the hybrid's worth based on information for up to five traits. A maize breeder may utilize his or her own set of traits for the selection index. One of the traits that is almost always included is yield. The selection index data presented in the tables represent the mean value averaged across testing stations.

SELF POLLINATION. A plant is self-pollinated if pollen from one flower is transferred to the same or another flower of the same plant.

SIB POLLINATION. A plant is sib-pollinated when individuals within the same family or line are used for pollination.

SLFBLT=SOUTHERN LEAF BLIGHT (*Helminthosporium maydis* or *Bipolaris maydis*). A 1 to 9 visual rating indicating the resistance to Southern Leaf Blight. A higher score indicates a higher resistance.

SOURST=SOUTHERN RUST (*Puccinia polysora*). A 1 to 9 visual rating indicating the resistance to Southern Rust. A higher score indicates a higher resistance.

STAGRN=STAY GREEN. Stay green is the measure of plant health near the time of black layer formation (physiological maturity). A high score indicates better late-season plant health.

STDADV=STALK STANDING ADVANTAGE. The advantage of variety #1 over variety #2 for the trait STK CNT.

STKCNT=NUMBER OF PLANTS. This is the final stand or number of plants per plot.

STKLDG=STALK LODGING REGULAR. This is the percentage of plants that did not stalk lodge (stalk breakage) at regular harvest (when grain moisture is between about 20 and 30%) as measured by either natural lodging or pushing the stalks and determining the percentage of plants that break below the ear.

STKLDL=LATE STALK LODGING. This is the percentage of plants that did not stalk lodge (stalk breakage) at or around late season harvest (when grain moisture is between about 15 and 18%) as measured by either natural lodging or pushing the stalks and determining the percentage of plants that break below the ear.

STKLDS=STALK LODGING SCORE. A plant is considered as stalk lodged if the stalk is broken or crimped between the ear and the ground. This can be caused by any or a combination of the following: strong winds late in the season, disease pressure within the stalks, ECB damage or genetically weak stalks. This trait should be taken just prior to or at harvest. Expressed on a 1 to 9 scale with 9 being no lodging.

STLLPN=LATE STALK LODGING. This is the percent of plants that did not stalk lodge (stalk breakage or crimping) at or around late season harvest (when grain moisture is below 20%) as measured by either natural lodging or pushing the stalks and determining the percentage of plants that break or crimp below the ear.

STLPCN=STALK LODGING REGULAR. This is an estimate of the percentage of plants that did not stalk lodge (stalk breakage) at regular harvest (when grain moisture is between about 20 and 30%) as measured by either natural lodging or pushing the stalks and determining the percentage of plants that break below the ear.

STRT=GRAIN STARCH. Absolute value of starch content of the kernel as predicted by Near-Infrared Transmittance and expressed as a percent of dry matter.

STWWLT=Stewart's Wilt (*Erwinia stewartii*). A 1 to 9 visual rating indicating the resistance to Stewart's Wilt. A higher score indicates a higher resistance.

TASBLS=TASSEL BLAST. A 1 to 9 visual rating was used to measure the degree of blasting (necrosis due to heat stress) of the tassel at the time of flowering. A 1 would indicate a very high level of blasting at time of flowering, while a 9 would have no tassel blasting.

TASSZ=TASSEL SIZE. A 1 to 9 visual rating was used to indicate the relative size of the tassel. The higher the rating the larger the tassel.

TAS WT=TASSEL WEIGHT. This is the average weight of a tassel (grams) just prior to pollen shed.

TEXEAR=EAR TEXTURE. A 1 to 9 visual rating was used to indicate the relative hardness (smoothness of crown) of mature grain. A 1 would be very soft (extreme dent) while a 9 would be very hard (flinty or very smooth crown).

TILLER=TILLERS. A count of the number of tillers per plot that could possibly shed pollen was taken. Data are given as a percentage of tillers: number of tillers per plot divided by number of plants per plot.

TSTWT=TEST WEIGHT (UNADJUSTED). The measure of the weight of the grain in pounds for a given volume (bushel).

TSWADV=TEST WEIGHT ADVANTAGE. The test weight advantage of variety #1 over variety #2.

WIN M%=PERCENT MOISTURE WINS.

WIN Y%=PERCENT YIELD WINS.

YIELD BU/A=YIELD (BUSHELS/ACRE). Yield of the grain at harvest in bushels per acre adjusted to 15% moisture.

YLDADV=YIELD ADVANTAGE. The yield advantage of variety #1 over variety #2 as calculated by: YIELD of variety #1—YIELD variety #2=yield advantage of variety #1.

YLDSC=YIELD SCORE. A 1 to 9 visual rating was used to give a relative rating for yield based on plot ear piles. The higher the rating the greater visual yield appearance.

Definitions for Area of Adaptability

When referring to area of adaptability, such term is used to describe the location with the environmental conditions that would be well suited for this maize line. Area of adaptability is based on a number of factors, for example: days to maturity, insect resistance, disease resistance, and drought resistance. Area of adaptability does not indicate that the maize line will grow in every location within the area of adaptability or that it will not grow outside the area.

Central Corn Belt: Iowa, Illinois, Indiana

Drylands: non-irrigated areas of North Dakota, South Dakota, Nebraska, Kansas, Colorado and Oklahoma Eastern U.S.: Ohio, Pennsylvania, Delaware, Maryland, Virginia, and West Virginia North central U.S.: Minnesota and Wisconsin Northeast: Michigan, New York, Vermont, and Ontario and Quebec Canada Northwest U.S.: North Dakota, South Dakota, Wyoming, Washington, Oregon, Montana, Utah, and Idaho
South central U.S.: Missouri, Tennessee, Kentucky, Arkansas
Southeast U.S.: North Carolina, South Carolina, Georgia, Florida, Alabama, Mississippi, and Louisiana
Southwest U.S.: Texas, Oklahoma, New Mexico, Arizona
Western U.S.: Nebraska, Kansas, Colorado, and California
Maritime Europe: Northern France, Germany, Belgium, Netherlands and Austria

DETAILED DESCRIPTION OF THE INVENTION AND FURTHER EMBODIMENTS

All Tables Discussed in the Detailed Description of the Invention and Further Embodiments Section can Found at the End of the Section Morphological and Physiological Characteristics of PH8JR Inbred maize line PH8JR is a yellow, dent maize inbred with some flint characteristics that may be used as either a male or female in the production of the first generation F1 maize hybrids. Inbred maize line PH8JR is best adapted to the Central Corn Belt, Northwest, Northcentral, Northeast, Western and Drylands in the United States and Canada, and can be used to produce hybrids with approximately 102 maturity based on the Comparative Relative Maturity Rating System for harvest moisture of grain. Inbred maize line PH8JR demonstrates above average yield and good tassel size as an inbred per se. In hybrid combination, inbred PH8JR demonstrates high yield relative to moisture, strong roots, short plant height and low ear placement, above average brittle snap resistance.

The inbred has shown uniformity and stability within the limits of environmental influence for all the traits as described in the Variety Description Information (Table 1, found at the end of the section). The inbred has been self-pollinated and ear-rowed a sufficient number of generations with careful attention paid to uniformity of plant type to ensure the homozygosity and phenotypic stability necessary for use in commercial hybrid seed production. The line has been increased both by hand and in isolated fields with continued observation for uniformity. No variant traits have been observed or are expected in PH8JR.

Inbred maize line PH8JR, being substantially homozygous, can be reproduced by planting seeds of the line, growing the resulting maize plants under self-pollinating or sib-pollinating conditions with adequate isolation, and harvesting the resulting seed using techniques familiar to the agricultural arts.

Genotypic Characteristics of PH8JR

In addition to phenotypic observations, a plant can also be identified by its genotype. The genotype of a plant can be characterized through a genetic marker profile, which can identify plants of the same variety or a related variety, or be used to determine or validate a pedigree. The SSR profile of Inbred PH8JR can be found in Table 2 at the end of this section.

As a result of inbreeding, PH8JR is substantially homozygous. This homozygosity has been characterized at the loci shown in the marker profile provided herein. An F1 hybrid made with PH8JR would comprise the marker profile of PH8JR shown herein. This is because an F1 hybrid is the sum of its inbred parents, e.g., if one inbred parent is homozygous for allele x at a particular locus, and the other inbred parent is homozygous for allele y at that locus, the F1 hybrid will be x.y (heterozygous) at that locus. The profile can therefore be used to identify hybrids comprising PH8JR as a parent, since such hybrids will comprise two sets of alleles, one set of which will be from PH8JR. The determination of the male set of alleles and the female set of alleles may be made by profiling the hybrid and the pericarp of the hybrid seed, which is composed of maternal parent cells. The paternal parent profile is obtained by subtracting the pericarp profile from the hybrid profile.

Subsequent generations of progeny produced by selection and breeding are expected to be of genotype x (homozygous), y (homozygous), or x.y (heterozygous) for these locus positions. When the F1 plant is used to produce an inbred, the resulting inbred should be either x or y for that allele. In that regard, a unique allele or combination of alleles unique to that inbred can be used to identify progeny plants that retain those unique alleles or combinations of alleles.

Therefore, in accordance with the above, an embodiment of this invention is a PH8JR progeny maize plant or plant part that is a first generation hybrid maize plant comprising two sets of alleles, wherein one set of the alleles is the same as PH8JR at all of the SSR loci listed in Table 2. A maize cell wherein one set of the alleles is the same as PH8JR at all of the SSR loci listed in Table 2 is also an embodiment of the invention. This maize cell may be a part of a hybrid seed produced by crossing PH8JR with another inbred maize plant.

Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Berry, Don, et al., "Assessing Probability of Ancestry Using Simple Sequence Repeat Profiles: Applications to Maize Hybrids and Inbreds", Genetics, 2002, 161:813-824, and Berry, Don, et al., "Assessing Probability of Ancestry Using Simple Sequence Repeat Profiles: Applications to Maize Inbred Lines and Soybean Varieties", Genetics, 2003, 165: 331-342, which are incorporated by reference herein.

Particular markers used for these purposes are not limited to the set of markers disclosed herein, but may include any type of marker and marker profile which provides a means of distinguishing varieties. In addition to being used for identification of Inbred Line PH8JR, a hybrid produced through the use of PH8JR, and the identification or verification of pedigree for progeny plants produced through the use of PH8JR, the genetic marker profile is also useful in further breeding and in developing an introgressed trait conversion of PH8JR.

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by the polymerase chain reaction (PCR), thereby eliminating the need for labor-intensive Southern hybridization. The PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, comprise the major part of the methodology.

Following amplification, markers can be scored by electrophoresis of the amplification products. Scoring of marker genotype is based on the size of the amplified fragment, which may be measured by the base pair weight or molecular weight of the fragment. While variation in the primer used or in laboratory procedures can affect the reported fragment size, relative values should remain constant regardless of the specific primer or laboratory used. When comparing lines it is preferable if all SSR profiles are performed in the same lab. The SSR analyses reported herein were conducted in-house at Pioneer Hi-Bred. An SSR service is available to the public on a contractual basis by DNA Landmarks in Saint-Jean-sur-Richelieu, Quebec, Canada (formerly Paragen, Celera AgGen, Perkin-Elmer AgGen, Linkage Genetics and NPI).

Primers used for the SSRs reported herein are publicly available and may be found in the Maize GDB on the World Wide Web at maizegdb.org (sponsored by the USDA Agricultural Research Service), in Sharopova et al. (Plant Mol. Biol. 48(5-6):463-481), Lee et al (Plant Mol. Biol. 48(5-6); 453-461), or may be constructed from sequences if reported herein. Primers may be constructed from publicly available sequence information. Some marker information may also be available from DNA Landmarks.

Map information is provided by bin number as reported in the Maize GDB for the IBM 2 and/or IBM 2 Neighbors maps. The bin number digits to the left of decimal point represent the chromosome on which such marker is located, and the digits to the right of the decimal represent the location on such chromosome. A bin number.xx designation indicates that the bin location on that chromosome is not known. Map positions are also available on the Maize GDB for a variety of different mapping populations.

PH8JR and its plant parts can be identified through molecular marker profile. An inbred corn plant cell having the SSR genetic marker profile shown in Table 2 is an embodiment of the invention. Such cell may be either diploid or haploid.

Also encompassed within the scope of the invention are plants and plant parts substantially benefiting from the use of PH8JR in their development, such as PH8JR comprising a introgressed trait through backcross conversion or transformation, and which may be identified by having an SSR molecular marker profile with a high percent identity to PH8JR, such as at least 80%, 81%, 82%, 83%, 84%, 85%, 86%, 87%, 88%, 89%, 90%, 91%, 92%, 93%, 94%, 95%, 96%, 97%, 98%, 99% or 99.5% identity. Likewise, percent similarity at these percentages may be used to identify hybrid and other non-inbred plants produced by the use of PH8JR.

An embodiment of this invention is an inbred PH8JR progeny maize plant or plant part comprising the same homozygous alleles as the plant or plant part of PH8JR for at least 90% of the SSR loci listed in Table 2. A plant cell comprising the same homozygous alleles as a plant cell of PH8JR for at least 90% of the SSR loci listed in Table 2 is also an embodiment of this invention. In these specific embodiments, 90% may also be replaced by any integer or partial integer percent of 80% or greater as listed above. One means of producing such a progeny plant, plant part or cell is through the backcrossing and/or transformation methods described herein.

Similarly, an embodiment of this invention is a PH8JR progeny maize plant or plant part comprising at least one allele per locus that is the same allele as the plant or plant part of PH8JR for at least 90% of the SSR loci listed in Table 2. This progeny plant may be a hybrid. A progeny or hybrid plant cell wherein at least one allele per locus that is the same allele as the plant cell PH8JR for at least 90% of the SSR loci listed in Table 2 is also a specific embodiment of this invention. In these specific embodiments, 90% may also be replaced by any integer percent listed above. One means of producing such a progeny or hybrid plant, plant part or cell is through the backcrossing and/or transformation methods described herein.

In addition, the SSR profile of PH8JR also can be used to identify essentially derived varieties and other progeny lines developed from the use of PH8JR, as well as cells and other plant parts thereof. Progeny plants and plant parts produced using PH8JR may be identified by having a molecular marker profile of at least 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 79%, 80%, 81%, 82%, 83%, 84%, 85%, 86%, 87%, 88%,89%, 90%, 91%, 92%, 93%, 94%, 95%, 96%, 97%, 98%, 99% or 99.5% genetic contribution from inbred line PH8JR, as measured by either percent identity or percent similarity.

Comparing PH8JR to other Inbreds

A breeder uses various methods to help determine which plants should be selected from segregating populations and ultimately which inbred lines will be used to develop hybrids for commercialization. In addition to knowledge of the germplasm and plant genetics, a part of the selection process is dependent on experimental design coupled with the use of statistical analysis. Experimental design and statistical analysis are used to help determine which plants, which family of plants, and finally which inbred lines and hybrid combinations are significantly better or different for one or more traits of interest. Experimental design methods are used to assess error so that differences between two inbred lines or two hybrid lines can be more accurately evaluated. Statistical analysis includes the calculation of mean values, determination of the statistical significance of the sources of variation, and the calculation of the appropriate variance components. Either a five or a one percent significance level is customarily used to determine whether a difference that occurs for a given trait is real or due to the environment or experimental error. One of ordinary skill in the art of plant breeding would know how to evaluate the traits of two plant varieties to determine if there is no significant difference between the two traits expressed by those varieties. For example, see Fehr, Walt, Principles of Cultivar Development, p. 261-286 (1987) which is incorporated herein by reference. Mean trait values may be used to determine whether trait differences are significant. Trait values should preferably be measured on plants grown under the same environmental conditions, and environmental conditions should be appropriate for the traits or traits being evaluated. Sufficient selection pressure should be present for optimum measurement of traits of interest such as herbicide, insect or disease resistance. Similarly, an introgressed trait conversion of PH8JR for resistance, such as herbicide resistance, should not be compared to PH8JR in the presence of the herbicide when comparing non-resistance related traits such as plant height and yield.

In Table 3, data from traits and characteristics of inbred maize line PH8JR per se are given and compared to other maize inbred lines and hybrids. The following are the results of these comparisons:

The results in Table 3A compare inbred PH8JR to inbred PH1 B8. The results show inbred PH8JR has significantly higher yield, lower moisture, and decreased tassel size compared to PH1 B8.

The results in Table 3B compare inbred PH8JR to inbred PH24E. The results show inbred PH8JR has significantly different pollen weight and ear height when compared to inbred PH24E.

The results in Table 3C compare inbred PH8JR to inbred PH7CP. The results show inbred PH8JR differs significantly from PH7CP in a number of traits including the number of growing degree units required to achieve 50% pollen shed, early growth, pollen weight and plant height.

Development of Maize Hybrids Using PH8JR

A single cross maize hybrid results from the cross of two inbred lines, each of which has a genotype that complements the genotype of the other. The hybrid progeny of the first generation is designated F1. In the development of commercial hybrids in a maize plant breeding program, only the F1 hybrid plants are sought. F1 hybrids are more vigorous than their inbred parents. This hybrid vigor, or heterosis, can be manifested in many polygenic traits, including increased vegetative growth and increased yield.

PH8JR may be used to produce hybrid maize. One such embodiment is the method of crossing inbred maize line PH8JR with another maize plant, such as a different maize inbred line, to form a first generation F1 hybrid seed. The first generation F1 hybrid seed, plant and plant part produced by this method is an embodiment of the invention. The first generation F1 seed, plant and plant part will comprise an essentially complete set of the alleles of inbred line PH8JR. One of ordinary skill in the art can utilize either breeder books or molecular methods to identify a particular F1 hybrid plant produced using inbred line PH8JR. Further, one of ordinary skill in the art may also produce F1 hybrids with transgenic, male sterile and/or backcross conversions of inbred line PH8JR.

The development of a maize hybrid in a maize plant breeding program involves three steps: (1) the selection of plants from various germplasm pools for initial breeding crosses; (2) the selfing of the selected plants from the breeding crosses for several generations to produce a series of inbred lines, such as PH8JR, which, although different from each other, breed true and are highly uniform; and (3) crossing the selected inbred lines with different inbred lines to produce the hybrids. During the inbreeding process in maize, the vigor of the lines decreases, and so one would not be likely to use PH8JR directly to produce grain. However, vigor is restored when PH8JR is crossed to a different inbred line to produce a commercial F1 hybrid. An important consequence of the homozygosity and homogeneity of the inbred line is that the hybrid between a defined pair of inbreds may be reproduced indefinitely as long as the homogeneity of the inbred parents is maintained.

PH8JR may be used to produce a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B)×(C×D). A three-way cross hybrid is produced from three inbred lines where two of the inbred lines are crossed (A×B) and then the resulting F1 hybrid is crossed with the third inbred (A×B)×C. In each case, pericarp tissue from the female parent will be a part of and protect the hybrid seed.

Combining Ability of PH8JR

Combining ability of a line, as well as the performance of the line per se, is a factor in the selection of improved maize inbreds. Combining ability refers to a line's contribution as a parent when crossed with other lines to form hybrids. The hybrids formed for the purpose of selecting superior lines may be referred to as test crosses, and include comparisons to other hybrid varieties grown in the same environment (same cross, location and time of planting). One way of measuring combining ability is by using values based in part on the overall mean of a number of test crosses weighted by number of experiment and location combinations in which the hybrid combinations occurs. The mean may be adjusted to remove environmental effects and known genetic relationships among the lines.

General combining ability provides an overall score for the inbred over a large number of test crosses. Specific combining ability provides information on hybrid combinations formed by PH8JR and a specific inbred parent. A line such as PH8JR which exhibits good general combining ability may be used in a large number of hybrid combinations.

A general combining ability report for inbred PH8JR is provided in Table 4. This data represents the overall mean value for these traits over hundreds of test crosses. Table 4 demonstrates that inbred PH8JR shows good general combining ability for hybrid production.

Hybrid Comparisons

These hybrid comparisons represent specific hybrid crosses with PH8JR and a comparison of these specific hybrids with other hybrids with favorable characteristics. These comparisons illustrate the good specific combining ability of PH8JR.

The results in Table 5A compare a specific hybrid for which inbred PH8JR is a parent and a second hybrid, 35Y54. The results show that the hybrid containing IS inbred PH8JR produced significantly different results over multiple traits including yield, moisture and number of growing degree units required to achieve 50% pollen shed.

The results in Table 5B compare a specific hybrid for which inbred PH8JR is a parent and a second hybrid, 35P12. The results show that the hybrid containing inbred PH8JR produced significantly different results over multiple traits including yield, moisture and number of growing degree units required to achieve 50% pollen shed.

The results in Table 5C compare a specific hybrid for which inbred PH8JR is a parent and a second hybrid, 36N70. The results show that the hybrid containing inbred PH8JR produced significantly different results over multiple traits including yield and plant height.

Introgression of a New Locus or Trait Into PH8JR.

PH8JR represents a new base genetic line into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of PH8JR

A backcross conversion of PH8JR occurs when DNA sequences are introduced through backcrossing (Hallauer et al, 1988), with PH8JR utilized as the recurrent parent. Both naturally occurring and transgenic DNA sequences may be introduced through backcrossing techniques. A backcross conversion may produce a plant with a trait or locus conversion in at least one or more backcrosses, including at least 2 crosses, at least 3 crosses, at least 4 crosses, at least 5 crosses and the like. Molecular marker assisted breeding or selection may be utilized to reduce the number of backcrosses necessary to achieve the backcross conversion. For example, see Openshaw, S. J. et al., Marker-assisted Selection in Backcross Breeding. In: Proceedings Symposium of the Analysis of Molecular Data, August 1994, Crop Science Society of America, Corvallis, Oreg., where it is demonstrated that a backcross conversion can be made in as few as two backcrosses.

The complexity of the backcross conversion method depends on the type of trait being transferred (single genes or closely linked genes as vs. unlinked genes), the level of expression of the trait, the type of inheritance (cytoplasmic or nuclear) and the types of parents included in the cross. It is understood by those of ordinary skill in the art that for single gene traits that are relatively easy to classify, the backcross method is effective and relatively easy to manage. (See Hallauer et al. in Corn and Corn Improvement, Sprague and Dudley, Third Ed. 1998). Desired traits that may be transferred through backcross conversion include, but are not limited to, waxy starch, sterility (nuclear and cytoplasmic), fertility restoration, grain color (white), nutritional enhancements, drought tolerance, nitrogen utilization, altered fatty acid profile, increased digestibility, low phytate, industrial enhancements, disease resistance (bacterial, fungal or viral), insect resistance, herbicide resistance and yield enhancements. In addition, an introgression site itself, such as an FRT site, Lox site or other site specific integration site, may be inserted by backcrossing and utilized for direct insertion of one or more genes of interest into a specific plant variety. In some embodiments of the invention, the number of loci that may be backcrossed into PH8JR is at least 1, 2, 3, 4, or 5 and/or no more than 6, 5, 4, 3, or 2. A single loci may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes transferred via backcrossing typically function as a dominant single gene trait and are relatively easy to classify. Selection of progeny for a trait that is transferred via a recessive allele, such as the waxy starch characteristic, requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Along with selection for the trait of interest, progeny are selected for the phenotype of the recurrent parent. While occasionally additional polynucleotide sequences or genes may be transferred along with the backcross conversion, the backcross conversion line "fits into the same hybrid combination as the recurrent parent inbred line and contributes the effect of the additional gene added through the backcross." Poehlman et al. (1995, page 334). It has been proposed that in general there should be at least four backcrosses when it is important that the recovered lines be essentially identical to the recurrent parent except for the characteristic being transferred (Fehr 1987, Principles of Cultivar Development). However, as noted above, the number of backcrosses necessary can be reduced with the use of molecular markers. Other factors, such as a genetically similar donor parent, may also reduce the number of backcrosses necessary.

One process for adding or modifying a trait or locus in maize inbred line PH8JR comprises crossing PH8JR plants grown from PH8JR seed with plants of another maize line that comprise the desired trait or locus, selecting F1 progeny plants that comprise the desired trait or locus to produce selected F1 progeny plants, crossing the selected progeny plants with the PH8JR plants to produce backcross progeny plants, selecting for backcross progeny plants that have the desired trait or locus and the morphological characteristics of maize inbred line PH8JR to produce selected backcross progeny plants; and backcrossing to PH8JR three or more times in succession to produce selected fourth or higher backcross progeny plants that comprise said trait or locus. The modified PH8JR may be further characterized as having the physiological and morphological characteristics of maize inbred line PH8JR listed in Table 1 as determined at the 5% significance level when grown in the same environmental conditions and/or may be characterized by percent similarity or identity to PH8JR as determined by SSR markers. The above method may be utilized with fewer backcrosses in appropriate situations, such as when the donor parent is highly related or markers are used in the selection step. Desired traits that may be used include those nucleic acids known in the art, some of which are listed herein, that will affect traits through nucleic acid expression or inhibition. Desired loci include the introgression of FRT, Lox and other sites for site specific integration, which may also affect a desired trait if a functional nucleic acid is inserted at the integration site.

In addition, the above process and other similar processes described herein may be used to produce F1 hybrid maize seed by adding a step at the end of the process that comprises crossing PH8JR with the introgressed trait or locus with a different maize plant and harvesting the resultant F1 hybrid maize seed.

Male Sterility and Hybrid Seed Production

Hybrid seed production requires elimination or inactivation of pollen produced by the female inbred parent. Incomplete removal or inactivation of the pollen provides the potential for self-pollination. A reliable method of controlling male fertility in plants offers the opportunity for improved seed production.

PH8JR can be produced in a male-sterile form. There are several ways in which a maize plant can be manipulated so that it is male sterile. These include use of manual or mechanical emasculation (or detasseling), use of one or more genetic factors that confer male sterility, including cytoplasmic genetic and/or nuclear genetic male sterility, use of gametocides and the like. A male sterile inbred designated PH8JR may include one or more genetic factors, which result in cytoplasmic genetic and/or nuclear genetic male sterility. All of such embodiments are within the scope of the present claims. The male sterility may be either partial or complete male sterility.

Hybrid maize seed is often produced by a male sterility system incorporating manual or mechanical detasseling. Alternate strips of two maize inbreds are planted in a field, and the pollen-bearing tassels are removed from one of the inbreds (female). Provided that there is sufficient isolation from sources of foreign maize pollen, the ears of the detasseled inbred will be fertilized only from the other inbred (male), and the resulting seed is therefore hybrid and will form hybrid plants.

The laborious detasseling process can be avoided by using cytoplasmic male-sterile (CMS) inbreds. Plants of a CMS inbred are male sterile as a result of genetic factors in the cytoplasm, as opposed to the nucleus, and so nuclear linked genes are not transferred during backcrossing. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile, and either option may be preferred depending on the intended use of the hybrid. The same hybrid seed, a portion produced from detasseled fertile maize and a portion produced using the CMS system, can be blended to insure that adequate pollen loads are available for fertilization when the hybrid plants are grown. CMS systems have been successfully used since the 1950's, and the male sterility trait is routinely backcrossed into inbred lines. See Wych, p. 585-586, 1998.

There are several methods of conferring genetic male sterility available, such as multiple mutant genes at separate locations within the genome that confer male sterility, as disclosed in U.S. Pat. Nos. 4,654,465 and 4,727,219 to Brar et al. and chromosomal translocations as described by Patterson in U.S. Pat. Nos. 3,861,709 and 3,710,511. In addition to these methods, Albertsen et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

These, and the other methods of conferring genetic male sterility in the art, each possess their own benefits and drawbacks. Some other methods use a variety of approaches such as delivering into the plant a gene encoding a cytotoxic substance associated with a male tissue specific promoter or an antisense system in which a gene critical to fertility is identified and an antisense to that gene is inserted in the plant (see: Fabinjanski, et al. EPO 89/3010153.8 publication no. 329, 308 and PCT application PCT/CA90/00037 published as WO 90/08828).

Another system for controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see Carlson, Glenn R., U.S. Pat. No. 4,936,904). Application of the gametocide, timing of the application and genotype specificity often limit the usefulness of the approach and it is not appropriate in all situations.

Incomplete control over male fertility may result in self-pollinated seed being unintentionally harvested and packaged with hybrid seed. This would typically be only female parent seed, because the male plant is grown in rows that are typically destroyed prior to seed development. Once the seed from the hybrid bag is planted, it is possible to identify and select these self-pollinated plants. These self-pollinated plants will be genetically equivalent to one of the inbred lines used to produce the hybrid. Though the possibility of inbred PH8JR being included in a hybrid seed bag exists, the occurrence is very low because much care is taken by seed companies to avoid such inclusions. It is worth noting that hybrid seed is sold to growers for the production of grain or forage and not for breeding or seed production. These self-pollinated plants can be identified and selected by one skilled in the art due to their less vigorous appearance for vegetative and/or reproductive characteristics, including shorter plant height, small ear size, ear and kernel shape, cob color, or other characteristics.

Identification of these self-pollinated lines can also be accomplished through molecular marker analyses. See, "The Identification of Female Selfs in Hybrid Maize: A Comparison Using Electrophoresis and Morphology", Smith, J. S. C. and Wych, R. D., Seed Science and Technology 14, pp. 1-8 (1995), the disclosure of which is expressly incorporated herein by reference. Through these technologies, the homozygosity of the self pollinated line can be verified by analyzing allelic composition at various loci along the genome. Those methods allow for rapid identification of the invention disclosed herein. See also, "Identification of Atypical Plants in Hybrid Maize Seed by Postcontrol and Electrophoresis" Sarca, V. et al., Probleme de Genetica Teoritica si Aplicata Vol. 20 (1) p. 29-42.

An embodiment of this invention is a process for producing seed of PH8JR, comprising planting a collection of seed comprising seed of a hybrid, one of whose parents is inbred PH8JR, said collection also comprising seed of said inbred, growing plants from said collection of seed, identifying inbred parent plants, selecting said inbred parent plant; and controlling pollination to preserve the homozygosity of said inbred parent plant.

Transformation

The advent of new molecular biological techniques has allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, that are inserted into the genome using transformation are referred to herein collectively as "transgenes". In some embodiments of the invention, a transformed variant of PH8JR may contain at least one transgene but could contain at least 1, 2, 3, 4, 5, 6, 7, 8, 9, 10 and/or no more than 15, 14, 13, 12, 11, 10, 9, 8, 7, 6, 5, 4, 3, or 2. Over the last fifteen to twenty years several methods for producing transgenic plants have been developed, and the present invention also relates to transformed versions of the claimed inbred maize line PH8JR as well as hybrid combinations thereof.

Numerous methods for plant transformation have been developed, including biological and physical plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88 and Armstrong, "The First Decade of Maize Transformation: A Review and Future Perspective" (Maydica 44:101-109, 1999). In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into the genome of a particular maize plant using transformation techniques, could be moved into the genome of another line using traditional breeding techniques that are well known in the plant breeding arts. For example, a backcrossing approach is commonly used to move a transgene from a transformed maize plant to an elite inbred line, and the resulting progeny would then comprise the transgene(s). Also, if an inbred line was used for the transformation then the transgenic plants could be crossed to a different inbred in order to produce a transgenic hybrid maize plant.

Various genetic elements can be introduced into the plant genome using transformation. These elements include, but are not limited to genes; coding sequences; inducible, constitutive, and tissue specific promoters; enhancing sequences; and signal and targeting sequences. For example, see the traits, genes and transformation methods listed in U.S. Pat. No. 6,118,055.

With transgenic plants according to the present invention, a foreign protein can be produced in commercial quantities. Thus, techniques for the selection and propagation of transformed plants, which are well understood in the art, yield a plurality of transgenic plants that are harvested in a conventional manner, and a foreign protein then can be extracted from a tissue of interest or from total biomass. is Protein extraction from plant biomass can be accomplished by known methods which are discussed, for example, by Heney and Orr, Anal. Biochem. 114: 92-6 (1981).

A genetic map can be generated, primarily via conventional Restriction Fragment Length Polymorphisms (RFLP), Polymerase Chain Reaction (PCR) analysis, Simple Sequence Repeats (SSR) and Single Nucleotide Polymorphisms (SNP) that identifies the approximate chromosomal location of the integrated DNA molecule. For exemplary methodologies in this regard, see Glick and Thompson, METHODS IN PLANT MOLECULAR BIOLOGY AND BIOTECHNOLOGY 269-284 (CRC Press, Boca Raton, 1993).

Wang et al. discuss "Large Scale Identification, Mapping and Genotyping of Single-Nucleotide Polymorphisms in the Human Genome", Science, 280:1077-1082, 1998, and similar capabilities are becoming increasingly available for the corn genome. Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant. Map comparisons would involve hybridizations, RFLP, PCR, SSR and sequencing, all of which are conventional techniques. SNPs may also be used alone or in combination with other techniques.

Likewise, by means of the present invention, plants can be genetically engineered to express various phenotypes of agronomic interest. Through the transformation of maize the expression of genes can be modulated to enhance disease resistance, insect resistance, herbicide resistance, agronomic, grain quality and other traits. Transformation can also be used to insert DNA sequences which control or help control male-sterility. DNA sequences native to maize as well as non-native DNA sequences can be transformed into maize and used to modulate levels of native or non-native proteins. Various promoters, targeting sequences, enhancing sequences, and other DNA sequences can be inserted into the maize genome for the purpose of modulating the expression of proteins. Reduction of the activity of specific genes (also known as gene silencing, or gene suppression) is desirable for several aspects of genetic engineering in plants.

Many techniques for gene silencing are well known to one of skill in the art, including but not limited to antisense technology (see, e.g., Sheehy et al. (1988) *PNAS USA* 85:8805-8809; and U.S. Pat. Nos. 5,107,065; 5,453, 566; and 5,759, 829); co-suppression (e.g., Taylor (1997) *Plant Cell* 9:1245; Jorgensen (1990) *Trends Biotech.* 8(12):340-344; Flavell (1994) *PNAS USA* 91:3490-3496; Finnegan et al. (1994) *Bio/Technology* 12: 883-888; and Neuhuber et al. (1994) *Mol. Gen. Genet.* 244:230-241); RNA interference (Napoli et al. (1990) *Plant Cell* 2:279-289; U.S. Pat. No. 5,034,323; Sharp (1999) *Genes Dev.* 13:139-141; Zamore et al. (2000) *Cell* 101:25-33; and Montgomery et al. (1998) *PNAS USA* 95:15502-15507), virus-induced gene silencing (Burton, et al. (2000) *Plant Cell* 12:691-705; and Baulcombe (1999) *Curr. Op. Plant Bio.* 2:109-113); target-RNA-specific ribozymes (Haseloff et al. (1988) *Nature* 334: 585-591); hairpin structures (Smith et al. (2000) *Nature* 407:319-320; WO 99/53050; and WO 98/53083); ribozymes (Steinecke et al. ((1992) *EMBO J.* 1 1:1525; and Perriman et al. ((1993) *Antisense Res. Dev.* 3:253); oligonucleotide mediated targeted modification (e.g., WO 03/076574 and WO 99/25853); Zn-finger targeted molecules (e.g., WO 01/52620; WO 03/048345; and WO 00/42219); and other methods or combinations of the above methods known to those of skill in the art.

Exemplary transgenes useful for genetic engineering include, but are not limited to, those categorized below.

1. Transgenes that Confer Resistance to Pests or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporum fulvum*); Martin et al., Science 262: 1432 (1993) (tomato Pto gene for resistance to *Pseudomonas syringae* pv. tomato encodes a protein kinase); Mindrinos et al., Cell 78: 1089 (1994) (*Arabidopsis* RSP2 gene for resistance to *Pseudomonas syringae*). A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Nos. 40098, 67136, 31995 and 31998. Other examples of *Bacillus thudngiensis* transgenes being genetically engineered are given in the following patents and patent applications and hereby are incorporated by reference for this purpose: U.S. Pat. Nos. 5,188,960; 5,689,052; 5,880,275; WO 91/114778; WO 99/31248; WO 01/12731; WO 99/24581; WO 97/40162 and U.S. application Ser. Nos. 10/032,717; 10/414,637; and 10/606,320.

(C) An insect-specific hormone or pheromone such as an ecdysteroid and juvenile hormone, a variant thereof, a mimetic based thereon, or an antagonist or agonist thereof.

See, for example, the disclosure by Hammock et al., *Nature* 344: 458 (1990), of baculovirus expression of cloned juvenile hormone esterase, an inactivator of juvenile hormone.

(D) An insect-specific peptide which, upon expression, disrupts the physiology of the affected pest. For example, see the disclosures of Regan, *J. Biol. Chem.* 269: 9 (1994) (expression cloning yields DNA coding for insect diuretic hormone receptor), and Pratt et al., *Biochem. Biophys. Res. Comm.* 163: 1243 (1989) (an allostatin is identified in *Diploptera puntata*). See also U.S. Pat. No. 5,266,317 to Tomalski et al., who disclose genes encoding insect-specific toxins.

(E) An enzyme responsible for an hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et at., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene.

(G) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(H) A hydrophobic moment peptide. See PCT application WO 95/16776 (disclosure of peptide derivatives of Tachyplesin which inhibit fungal plant pathogens) and PCT application WO 95/18855 (teaches synthetic antimicrobial peptides that confer disease resistance), the respective contents of which are hereby incorporated by reference for this purpose.

(I) A membrane permease, a channel former or a channel blocker. For example, see the disclosure by Jaynes et al., *Plant Sci.* 89: 43 (1993), of heterologous expression of a cecropin-beta lytic peptide analog to render transgenic s tobacco plants resistant to *Pseudomonas solanacearum*.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A virus-specific antibody. See, for example, Tavladoraki et al., *Nature* 366: 469 (1993), who show that transgenic plants expressing recombinant antibody genes are protected from virus attack.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See Lamb et al., *Biol/Technology* 10: 1436 (1992). The cloning and characterization of a gene which encodes a bean endopolygalacturonase-inhibiting protein is described by Toubart et al., *Plant J.* 2: 367 (1992).

(N) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, S., Current Biology, 5(2) (1995).

(P) Antifungal genes (Cornelissen and Melchers, Pi. Physiol. 101:709-712, (1993) and Parijs et al., Planta 183: 258-264, (1991) and Bushnell et al., Can. J. of Plant Path. 20(2):137-149 (1998).

(Q) Detoxification genes, such as for fumonisin, beauvericin, moniliformin and zearalenone and their structurally related derivatives. For example, see U.S. Pat. No. 5,792,931.

(R) Cystatin and cysteine proteinase inhibitors.

(S) Defensin genes. See WO03000863.

(T) Genes conferring resistance to nematodes. See WO 03/033651 and Urwin et. al., Planta 204:472-479 (1998).

2. Transgenes that Confer Resistance to a Herbicide, For Example:

(A) A herbicide that inhibits the growing point or meristem, such as an imidazolinone or a sulfonylurea. Exemplary genes in this category code for mutant ALS and AHAS enzyme as described, for example, by Lee et al., *EMBO J.* 7: 1241 (1988), and Miki et al., *Theor. Appl. Genet* 80: 449 (1990), respectively. See also, U.S. Pat. Nos. 5,605,011; 5,013,659; 5,141,870; 5,767,361; 5,731,180; 5,304,732; 4,761,373; 5,331,107; 5,928,937; and 5,378,824; and international publication WO 96/33270, which are incorporated herein by reference for this purpose.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cycloshexones (ACCase inhibitor-encoding genes). See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E; and 5,491,288; and international publications WO 97/04103; WO 97/04114; WO 00/66746; WO 01/66704; WO 00/66747 and WO 00/66748, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over expression of genes encoding glyphosate N-acetyltransferase. See, for example, U.S. application Ser. Nos. 60/244,385; 60/377,175 and 60/377,719. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European Patent No. 0 242 246 and 0 242 236 to Leemans et al. De Greef et al., *Bio/Technology* 7: 61 (1989), describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 B1; and 5,879,903, which are incorporated herein by reference for this purpose. Exemplary genes conferring resistance to phenoxy proprionic acids and cycloshexones, such as sethoxydim and haloxyfop, are the Acc1-S1, Acc1-S2 and Acc1-S3 genes described by Marshall et al., *Theor. Appl. Genet.* 83: 435 (1992).

(C) A herbicide that inhibits photosynthesis, such as a triazine (psbA and gs+ genes) and a benzonitrile (nitrilase gene). Przibilla et al., Plant Cell 3: 169 (1991), describe the transformation of *Chlamydomonas* with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., *Biochem. J.* 285: 173 (1992).

(D) Acetohydroxy acid synthase, which has been found to make plants that express this enzyme resistant to multiple types of herbicides, has been introduced into a variety of plants (see, e.g., Hattori et al. (1995) Mol Gen Genet 246: 419). Other genes that confer tolerance to herbicides include: a gene encoding a chimeric protein of rat cytochrome P4507A1 and yeast NADPH-cytochrome P450 oxidoreductase (Shiota et al. (1994) Plant PhysiolPlant Physiol 106:17), genes for glutathione reductase and superoxide dismutase (Aono et al. (1995) Plant Cell Physiol 36:1687, and genes for various phosphotransferases (Datta et al. (1992) Plant Mol Biol 20:619).

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1; and 5,767,373; and international publication WO 01/12825, which are incorporated herein by reference for this purpose.

3. Transgenes that Confer or Contribute to a Grain Trait, Such As:

(A) Modified fatty acid metabolism, for example, by (1) Transforming a plant with an antisense gene of stearoyl-ACP desaturase to increase stearic acid content of the plant. See Knultzon et al., *Proc. Natl. Acad. Sci. USA* 89: 2624 (1992), (2) Elevating oleic acid via FAD-2 gene modification and/or decreasing linolenic acid via FAD-3 gene modification (see U.S. Pat. Nos. 6,063,947; 6,323,392; and WO 93/11245), (3) Altering conjugated linolenic or linoleic acid content, such as in WO 01/12800, (4) Modifying LEC1, AGP, Dek1, Superal1, thioredoxin, and/or a gamma zein knock out or mutant such as cs27 or TUSC 27. For example, see WO 02/42424, WO 98/22604, WO 03/011015, U.S. Pat. No. 6,423,886 and Rivera-Madrid, R. et. al. Proc. Natl. Acad. Sci. 92:5620-5624 (1995).

(B) Decreased phytate content, for example, by the (1) Introduction of a phytase-encoding gene would enhance breakdown of phytate, adding more free phosphate to the transformed plant. For example, see Van Hartingsveldt et al, *Gene* 127: 87 (1993), for a disclosure of the nucleotide sequence of an *Aspergillus niger* phytase gene.

(2) Introduction of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy et al., *Maydica* 35: 383 (1990) and/or by altering inositol kinase activity as in WO 02/059324, US2003/000901 1, WO 03/027243, US2003/0079247 and WO 99/05298.

(C) Modified carbohydrate composition effected, for example, by transforming plants with a gene coding for an enzyme that alters the branching pattern of starch. See Shiroza et al, *J. Bacteriol.* 170: 810 (1988) (nucleotide sequence of *Streptococcus mutans* fructosyltransferase gene), Steinmetz et al, *Mol. Gen. Genet.* 200: 220 (1985) (nucleotide sequence of *Bacillus subtilis* levansucrase gene), Pen et al, *Bio/Technology* 10: 292 (1992) (production of transgenic plants that express *Bacillus licheniformis* alpha-amylase), Elliot et al, *Plant Molec. Biol.* 21: 515 (1993) (nucleotide sequences of tomato invertase genes), Søgaard et al, *J. Biol. Chem.* 268: 22480 (1993) (site-directed mutagenesis of barley alpha-amylase gene), and Fisher et al, *Plant Physiol* 102: 1045 (1993) (maize endosperm starch branching enzyme II). The fatty acid modification genes mentioned above may also be used to effect starch content and/or composition through the interrelationship of the starch and oil pathways.

(D) Altered antioxidant content or composition, such as alteration of tocopherol or tocotrienols. For example, see WO 00/68393 involving the manipulation of antioxidant levels through alteration of a phytl prenyl transferase and WO 03/082899 through alteration of a homogentisate geranyl geranyl transferase.

(E) Improved digestibility and/or starch extraction through modification of UDP-D-xylose 4-epimerase, Fragile 1 and 2, Ref1, HCHL, C4H, such as in WO 99/10498.

4. Genes that Control Male-Sterility (A) Introduction of a deacetylase gene under the control of a tapetum-specific promoter and with the application of the chemical N-Ac-PPT (WO 01/29237).

(B) Introduction of various stamen-specific promoters (WO 92/13956, WO 92/13957).

(C) Introduction of the barnase and the barstar gene (Paul et al. Plant Mol. Biol. 19:611-622, 1992).

5. Genes that create a site for site specific DNA Integration. This includes the introduction of FRT sites that may be used in the FLP/FRT system and/or Lox sites that may be used in the Cre/Loxp system. For example, see Lyznik, et al., Site- Specific Recombination for Genetic Engineering in Plants, Plant Cell Rep (2003) 21:925-932 and WO 99/25821, which are hereby incorporated by reference. Other systems that may be used include the Gin recombinase of phage Mu (Maeser et al., 1991), the Pin recombinase of *E. coli* (Enomoto et al., 1983), and the R/RS system of the pSR1 plasmid (Araki et al., 1992).

6. Genes that affect growth characteristics, such as drought tolerance and nitrogen utilization. For example, see WO 00/73475 where water use efficiency is modulated through alteration of malate.

Using PH8JR to Develop other Maize Inbreds

Inbred maize lines such as PH8JR are typically developed for use in the production of hybrid maize lines. However, inbred lines such as PH8JR also provide a source of breeding material that may be used to develop new maize inbred lines. Plant breeding techniques known in the art and used in a maize plant breeding program include, but are not limited to, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of maize hybrids in a maize plant breeding program requires, in general, the development of homozygous inbred lines, the crossing of these lines, and the evaluation of the crosses. There are many analytical methods available to evaluate the result of a cross. The oldest and most traditional method of analysis is the observation of phenotypic traits but genotypic analysis may also be used.

Using PH8JR In A Breeding Program

This invention is directed to methods for producing a maize plant by crossing a is first parent maize plant with a second parent maize plant wherein either the first or second parent maize plant is an inbred maize plant of the line PH8JR. The other parent may be any other maize plant, such as another inbred line or a plant that is part of a synthetic or natural population. Any such methods using the inbred maize line PH8JR are part of this invention: selfing, sibbing, backcrosses, mass selection, pedigree breeding, bulk selection, hybrid production, crosses to populations, and the like. These methods are well known in the art and some of the more commonly used breeding methods are described below. Descriptions of breeding methods can also be found in one of several reference books (e.g., Allard, *Principles of Plant Breeding*, 1960; Simmonds, *Principles of Crop Improvement*, 1979; Fehr, "Breeding Methods for Cultivar Development", *Production and Uses*, $2^{nd}$ ed., Wilcox editor, 1987).

Pedigree Breeding

Pedigree breeding starts with the crossing of two genotypes, such as PH8JR and one other elite inbred line having one or more desirable characteristics that is lacking or which complements PH8JR. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection is practiced: F1→F2; F2→F3; F3→F4; F4→$F_5$, etc. After a sufficient amount of inbreeding, successive filial generations will serve to increase seed of the developed inbred. Preferably, the inbred line comprises homozygous alleles at about 95% or more of its loci.

In addition to being used to create a backcross conversion, backcrossing can also be used in combination with pedigree breeding to modify PH8JR and a hybrid that is made using the modified PH8JR. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of maize inbred line PH8JR, comprising the steps of crossing a plant of maize inbred line PH8JR with a donor plant comprising a mutant gene or transgene conferring a desired trait, selecting an F1 progeny plant comprising the mutant gene or transgene conferring the desired trait, and backcrossing the selected F1 progeny plant to a plant of maize inbred line PH8JR. This method may further comprise the step of obtaining a molecular marker profile of maize inbred line PH8JR and using the molecular marker profile to select for a progeny plant with the desired trait and the molecular marker profile of PH8JR. In the same manner, this method may be used to produce an F1 hybrid seed by adding a final step of crossing the desired trait conversion of maize inbred line PH8JR with a different maize plant to make F1 hybrid maize seed comprising a mutant gene or transgene conferring the desired trait.

Recurrent Selection and Mass Selection

Recurrent selection is a method used in a plant breeding program to improve a population of plants. PH8JR is suitable for use in a recurrent selection program. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation Breeding

Mutation breeding is one of many methods that could be used to introduce new traits into PH8JR. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principals of Cultivar Development" Fehr, 1993 Macmillan Publishing Company the disclosure of which is incorporated herein by reference. In addition, mutations created in other lines may be used to produce a backcross conversion of PH8JR that comprises such mutation.

Breeding with Molecular Markers

Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing PH8JR.

Isozyme Electrophoresis and RFLPs as discussed in Lee, M., "Inbred Lines of Maize and Their Molecular Markers," The Maize Handbook, (Springer-Verlag, New York, Inc. 1994, at 423-432), have been widely used to determine genetic composition. Isozyme Electrophoresis has a relatively low number of available markers and a low number of allelic variants among maize inbreds. RFLPs allow more discrimination because they have a higher degree of allelic variation in maize and a larger number of markers can be found. Both of these methods have been eclipsed by SSRs as discussed in Smith et al., "An evaluation of the utility of SSR loci as molecular markers in maize (Zea mays L.): comparisons with data from RFLPs and pedigree", Theoretical and Applied Genetics (1997) vol. 95 at 163-173 and by Pejic et al., "Comparative analysis of genetic similarity among maize inbreds detected by RFLPs, RAPDs, SSRs, and AFLPs," Theoretical and Applied Genetics (1998) at 1248-1255 incorporated herein by reference. SSR technology is more efficient and practical to use than RFLPs; more marker loci can be routinely used and more alleles per marker locus can be found using SSRs in comparison to RFLPs. Single Nucleotide Polymorphisms may also be used to identify the unique genetic composition of the invention and progeny lines retaining that unique genetic composition. Various molecular marker techniques may be used in combination to enhance overall resolution.

Maize DNA molecular marker linkage maps have been rapidly constructed and widely implemented in genetic studies. One such study is described in Boppenmaier, et al., "Comparisons among strains of inbreds for RFLPs", Maize Genetics Cooperative Newsletter, 65:1991, pg. 90, is incorporated herein by reference.

One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection.

Production of Double Haploids

The production of double haploids can also be used for the development of inbreds in the breeding program. For example, an F1 hybrid for which PH8JR is a parent can be used to produce double haploid plants. Double haploids are produced by the doubling of a set of chromosomes (1 N) from a heterozygous plant to produce a completely homozygous individual. For example, see Wan et al., "Efficient Production of Doubled Haploid Plants Through Colchicine Treatment of Anther-Derived Maize Callus", Theoretical and Applied Genetics, 77:889-892, 1989 and US2003/0005479. This can be advantageous because the process omits the generations of selfing needed to obtain a homozygous plant from a heterozygous source.

Thus, an embodiment of this invention is a process for making a substantially homozygous PH8JR progeny plant by producing or obtaining a seed from the cross of PH8JR and another maize plant and applying double haploid methods to the F1 seed or F1 plant or to any successive filial generation. Such methods decrease the number of generations required to produce an inbred with similar genetics or characteristics to PH8JR. See Bernardo, R. and Kahler, A. L., Theor. Appl. Genet. 102:986-992, 2001.

In particular, a process of making seed retaining the molecular marker profile of maize inbred line PH8JR is contemplated, such process comprising obtaining or producing F1 hybrid seed for which maize inbred line PH8JR is a parent, inducing doubled haploids to create progeny without the occurrence of meiotic segregation, obtaining the molecular marker profile of maize inbred line PH8JR, and selecting progeny that retain the molecular marker profile of PH8JR.

Use Of PH8JR In Tissue Culture

This invention is also directed to the use of PH8JR in tissue culture. As used herein, the term "tissue culture" includes plant protoplasts, plant cell tissue culture, cultured microspores, plant calli, plant clumps, and the like. As used herein, phrases such as "growing the seed" or "grown from the seed" include embryo rescue, isolation of cells from seed for use in tissue culture, as well as traditional growing methods.

Duncan, Williams, Zehr, and Widholm, Planta (1985) 165: 322-332 reflects that 97% of the plants cultured that produced callus were capable of plant regeneration. 10 Subsequent experiments with both inbreds and hybrids produced 91% regenerable callus that produced plants. In a further study in 1988, Songstad, Duncan & Widholm in *Plant Cell Reports* (1988), 7:262-265 reports several media additions that enhance regenerability of callus of two inbred lines. Other published reports also indicated that "nontraditional" tissues are capable of producing somatic embryogenesis and plant regeneration. K. P. Rao, et al., *Maize Genetics Cooperation Newsletter*, 60:64-65 (1986), refers to somatic embryogenesis from glume callus cultures and B. V. Conger, et al., *Plant Cell Reports*, 6:345-347 (1987) indicates somatic embryogenesis from the tissue cultures of maize leaf segments. Thus, it is clear from the literature that the state of the art is such that these methods of obtaining plants are, and were, "conventional" in the sense that they are routinely used and have a very high rate of success.

Tissue culture of maize, including tassel/anther culture, is described in U.S. 2002/0062506A1 and European Patent Application, publication 160,390, each of which are incorporated herein by reference for this purpose. Maize tissue culture procedures are also described in Green and Rhodes, "Plant Regeneration in Tissue Culture of Maize," *Maize for Biological Research* (Plant Molecular Biology Association, Charlottesville, Va. 1982, at 367-372) and in Duncan, et al., "The Production of Callus Capable of Plant Regeneration from Immature Embryos of Numerous *Zea Mays* Genotypes," 165 *Planta* 322-332 (1985). Thus, another aspect of this invention is to provide cells which upon growth and differentiation produce maize plants having the genotype and/or physiological and morphological characteristics of inbred line PH8JR.

Progeny Plants

All plants produced by the use of the methods described herein and that retain the unique genetic or trait combinations of PH8JR are within the scope of the invention. Progeny of the breeding methods described herein may be characterized in any number of ways, such as by traits retained in the progeny, pedigree and/or molecular markers. Combinations of these methods of characterization may be used.

Breeder's of ordinary skill in the art have developed the concept of an "essentially derived variety", which is defined in 7 U.S.C. § 2104(a)(3) of the Plant Variety Protection Act and is hereby incorporated by reference. Varieties and plants that are essentially derived from PH8JR are within the scope of the invention.

Pedigree is a method used by breeders of ordinary skill in the art to describe the varieties. Varieties that are more closely related by pedigree are likely to share common genotypes and combinations of phenotypic characteristics. All breeders of ordinary skill in the art maintain pedigree records of their breeding programs. These pedigree records contain a detailed description of the breeding process, including a listing of all parental lines used in the breeding process and information on how such line was used. One embodiment of this invention is progeny plants and parts thereof with at least one ancestor that is PH8JR, and more specifically, where the pedigree of the progeny includes 1, 2, 3, 4, and/or 5 or less breeding crosses to a maize plant other than PH8JR or a plant that has PH8JR as a parent or other progenitor. A breeder of ordinary skill in the art would know if PH8JR were used in the development of a progeny line, and would also know how many crosses to a line other than PH8JR or line with PH8JR as a parent or other progenitor were made in the development of any progeny line.

Molecular markers also provide a means by which those of ordinary skill in the art characterize the similarity or differences of two lines. Using the breeding methods described herein, one can develop individual plants, plant cells, and populations of plants that retain at least 25%, 30%, 35%, 40%, 45%, 50%, 55%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from inbred line PH8JR, as measured by either percent identity or percent similarity. In pedigree analysis the percentage genetic contribution may not be actually known, but on average 50% of the starting germplasm would be expected to be passed to the progeny line after one cross to another line, 25% after another cross to a different line, and so on. With backcrossing, the expected contribution of PH8JR after 2, 3, 4 and 5 doses (or 1, 2, 3 and 4 backcrosses) would be 75%, 87.5%, 93.75% and 96.875% respectively. Actual genetic contribution may be much higher than the genetic contribution expected by pedigree, especially if molecular markers are used in selection. Molecular markers could also be used to confirm and/or determine the pedigree of the progeny line.

Traits are also used by those of ordinary skill in the art to characterize progeny. Traits are commonly evaluated at a significance level, such as a 1%, 5% or 10% significance level, when measured in plants grown in the same environmental conditions. For example, a backcross conversion of PH8JR may be characterized as having the same morphological and physiological traits as PH8JR. The traits used for comparison may be any or all of the traits shown in Table 1, Table 3, Table 4 or Table 5.

A breeder will commonly work to combine a specific trait of an undeveloped variety of the species, such as a high level of resistance to a particular disease, with one or more of the elite agronomic characteristics (yield, maturity, plant size, lodging resistance, etc.) needed for use as a commercial variety. This combination, once developed, provides a valuable source of new germplasm for further breeding. For example, it may take 10-15 years and significant effort to produce such a combination, yet progeny may be developed that retain this combination in as little as 2-5 years and with much less effort.

SPECIFIC EMBODIMENTS

Specific methods and products produced using inbred line PH8JR in plant breeding are discussed in the following sections. The methods outlined are described in detail by way of illustration and example for purposes of clarity and understanding. However, it will be obvious that certain changes and modifications may be practiced within the scope of the invention.

One method for producing a line derived from inbred line PH8JR is as follows. One of ordinary skill in the art would produce or obtain a seed from the cross between inbred line PH8JR and another variety of maize, such as an elite inbred variety. The F1 seed derived from this cross would be grown to form a homogeneous population. The F1 seed would contain essentially all of the alleles from variety PH8JR and essentially all of the alleles from the other maize variety. The F1 nuclear genome would be made-up of 50% variety PH8JR and 50% of the other elite variety. The F1 seed would be grown and allowed to self, thereby forming F2 seed. On average the F2 seed would have derived 50% of its alleles from variety PH8JR and 50% from the other maize variety, but many individual plants from the population would have a greater percentage of their alleles derived from PH8JR (Wang J. and R. Bernardo, 2000, Crop Sci. 40:659-665 and Bernardo, R. and A. L. Kahler, 2001, Theor. Appl. Genet 102: 986-992). The molecular markers of PH8JR could be used to select and retain those lines with high similarity to PH8JR. The F2 seed would be grown and selection of plants would be made based on visual observation, markers and/or measurement of traits. The traits used for selection may be any PH8JR trait described in this specification, including the inbred per se maize PH8JR traits described herein under the detailed description of inbred PH8JR. Such traits may also be the good general or specific combining ability of PH8JR, including its ability to produce hybrids with the approximate maturity and/or hybrid combination traits described herein under the detailed description of inbred PH8JR. The PH8JR progeny plants that exhibit one or more of the desired PH8JR traits, such as those listed herein, would be selected and each plant would be harvested separately. This F3 seed from each plant would be grown in individual rows and allowed to self. Then selected rows or plants from the rows would be harvested individually. The selections would again be based on visual observation, markers and/or measurements for desirable traits of the plants, such as one or more of the desirable PH8JR traits listed herein. The process of growing and selection would be repeated any number of times until a PH8JR progeny inbred plant is obtained. The PH8JR progeny inbred plant would contain desirable traits derived from inbred plant PH8JR, some of which may not have been expressed by the other maize variety to which inbred line PH8JR was crossed and some of which may have been expressed by both maize varieties but now would be at a level equal to or greater than the level expressed in inbred variety PH8JR. However, in each case the resulting progeny line would benefit from the efforts of the inventor(s), and would not have existed but for the inventor(s) work in creating PH8JR. The PH8JR progeny inbred plants would have, on average, 50% of their nuclear genes derived from inbred line PH8JR, but many individual plants from the population would have a greater percentage of their alleles derived from PH8JR. This breeding cycle, of crossing and selfing, and optional selection, may be repeated to produce another population of PH8JR progeny maize plants with, on average, 25% of their nuclear genes derived from inbred line PH8JR, but, again, many individual plants from the population would have a greater percentage of their alleles derived from PH8JR. This process can be repeated for a third, fourth, fifth, sixth, seventh or more breeding cycles. Another embodiment of the invention is a PH8JR progeny plant that has received the desirable PH8JR traits listed herein through the use of PH8JR, which traits were not exhibited by other plants used in the breeding process.

Therefore, an embodiment of this invention is a PH8JR progeny maize plant, wherein at least one ancestor of said PH8JR progeny maize plant is the maize plant or plant part of PH8JR, and wherein the pedigree of said PH8JR progeny maize plant is within two breeding crosses of PH8JR or a plant that has PH8JR as a parent. The progeny plants, parts and plant cells produced from PH8JR may be further characterized as having a percent marker similarity or identity with PH8JR as described herein.

The previous example can be modified in numerous ways, for instance selection may or may not occur at every selfing generation, selection may occur before or after the actual self-pollination process occurs, or individual selections may be made by harvesting individual ears, plants, rows or plots at any point during the breeding process described. Double haploid breeding methods may be used at any step in the process. Instead of selfing out of the hybrid produced from the inbred, one could first cross the hybrid to either a parent line or a different inbred, and then self out of that cross.

The population of plants produced at each and any cycle of breeding is also an embodiment of the invention, and on average each such population would predictably consist of plants containing approximately 50% of its genes from inbred line PH8JR in the first breeding cycle, 25% of its genes from inbred line PH8JR in the second breeding cycle, 12.5% of its genes from inbred line PH8JR in the third breeding cycle, 6.25% in the fourth breeding cycle, 3.125% in the fifth breeding cycle, and so on. However, in each case the use of PH8JR provides a substantial benefit. The linkage groups of PH8JR would be retained in the progeny lines, and since current estimates of the maize genome size is about 50,000-80,000 genes (Xiaowu, Gai et al., Nucleic Acids Research, 2000, Vol. 28, No. 1, 94-96), in addition to non-coding DNA that impacts gene expression, it provides a significant advantage to use PH8JR as starting material to produce a line that retains desired genetics or traits of PH8JR.

Therefore, an embodiment of the invention is a process for making a population of PH8JR progeny inbred maize plants comprising obtaining or producing a first generation progeny maize seed comprising the plant of PH8JR as a parent, growing said first generation progeny maize seed to produce first generation maize plants and obtaining self or sib pollinated seed from said first generation maize plants, and growing the self or sib pollinated seed to obtain a population of PH8JR progeny inbred maize plants.

The population of PH8JR progeny inbred maize plants produced by this method are also embodiments of the invention, and such population as a whole will retain the expected genetic contribution of PH8JR. An inbred line selected from the population of PH8JR progeny inbred maize plants produced by this method is an embodiment, and such line may be further characterized by its molecular marker identity or similarity to PH8JR.

In this manner, the invention also encompasses a process for making a PH8JR inbred progeny maize plant comprising the steps of obtaining or producing a first generation progeny maize seed wherein a parent of said first generation progeny maize seed is a PH8JR plant, growing said first generation progeny maize seed to produce a first generation maize plant and obtaining self or sib pollinated seed from said first generation maize plant, and producing successive filial generations to obtain a PH8JR inbred progeny maize plant. Also an embodiment of this invention is the first breeding cycle inbred PH8JR maize plant produced by this method.

Crosses to Other Species

The utility of inbred maize line PH8JR also extends to crosses with other species. Commonly, suitable species will be of the family Graminaceae, and especially of the genera *Zea, Tripsacum, Coix, Schlerachne, Polytoca, Chionachne*, and *Trilobachne*, of the tribe Maydeae. Potentially suitable for crosses with PH8JR may be the various varieties of grain sorghum, *Sorghum bicolor* (L.) Moench.

INDUSTRIAL APPLICABILITY

Maize is used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications.

Plant parts other than the grain of maize are also used in industry: for example, stalks and husks are made into paper and wallboard and cobs are used for fuel and to make charcoal.

The seed of inbred maize line PH8JR, the plant produced from the inbred seed, the hybrid maize plant produced from the crossing of the inbred, hybrid seed, and various parts of the hybrid maize plant and transgenic versions of the foregoing, can be utilized for human food, livestock feed, and as a raw material in industry.

DEPOSITS

Applicants have made a deposit of at least 2500 seeds of Inbred Maize Line PH8JR with the American Type Culture Collection (ATCC), Manassas, Va. 20110 USA, ATCC Deposit No PTA-6357. The seeds deposited with the ATCC on Nov. 30, 2004 were taken from the deposit maintained by Pioneer Hi-Bred International, Inc., 7100 NW 62$^{nd}$ Avenue, Johnston, Ia. 50131-1000 since prior to the filing date of this application. Access to this deposit will be available during the pendency of the application to the Commissioner of Patents and Trademarks and persons determined by the Commissioner to be entitled thereto upon request. Upon allowance of any claims in the application, the Applicant(s) will make the deposit available to the public pursuant to 37 CFR 1.808. This deposit of the Inbred Maize Line PH8JR will be maintained in the ATCC depository, which is a public depository, for a period of 30 years, or 5 years after the most recent request, or for the enforceable life of the patent, whichever is longer, and will be replaced if it becomes is nonviable during that period. Additionally, Applicant has or will satisfy all the requirements of 37 C.F.R. §§1.801-1.809, including providing an indication of the viability of the sample upon deposit. Applicant has no authority to waive any restrictions imposed by law on the transfer of biological material or its transportation in commerce. Applicant does not waive any infringement of their rights granted under this patent or under the Plant Variety Protection Act (7 USC 2321 et seq.). U.S. Plant Variety Protection of Inbred Maize Line PH8JR has been applied for. Unauthorized seed multiplication is prohibited.

Tables

TABLE 1

| VARIETY DESCRIPTION INFORMATION VARIETY = PH8JR | | | |
|---|---|---|---|
|  | AVG | STDEV | N |
| 1. TYPE: (Describe intermediate types in comments section) | | | |
| 1 = Sweet, 2 = Dent, 3 = Flint, 4 = Flour, 5 = Pop and 6 = Ornamental. | 2 | | |
| Comments: Flint Like | | | |
| 2. MATURITY: DAYS HEAT UNITS | Days | H. Units | |
| Emergence to 50% of plants in silk | 59 | 1,251 | |
| Emergence to 50% of plants in pollen shed | 58 | 1,237 | |
| 10% to 90% pollen shed | 2 | 45 | |
| 50% Silk to harvest at 25% moisture | | | |
| 3. PLANT: | | | |
| Plant Height (to tassel tip) (cm) | 183.9 | 7.81 | 15 |
| Ear Height (to base of top ear node) (cm) | 71.5 | 8.94 | 15 |
| Length of Top Ear Internode (cm) | 13.7 | 1.98 | 15 |
| Average Number of Tillers per Plant | 0.0 | 0.00 | 3 |
| Average Number of Ears per Stalk | 1.1 | 0.02 | 3 |
| Anthocyanin of Brace Roots: 1 = Absent, 2 = Faint, 3 = Moderate, 4 = Dark | 2 | | |
| 4. LEAF: | | | |
| Width of Ear Node Leaf (cm) | 8.1 | 0.52 | 15 |
| Length of Ear Node Leaf (cm) | 75.9 | 3.98 | 15 |
| Number of Leaves above Top Ear | 5.5 | 0.64 | 15 |
| Leaf Angle: (at anthesis, 2nd leaf above ear to stalk above leaf) (Degrees) | 32.1 | 3.84 | 15 |
| * Leaf Color: V. Dark Green Munsell: 5GY34 | | | |
| Leaf Sheath Pubescence: 1 = none to 9 = like peach fuzz | 4 | | |
| 5. TASSEL: | | | |
| Number of Primary Lateral Branches | 9.2 | 2.04 | 15 |
| Branch Angle from Central Spike | 37.3 | 7.76 | 15 |
| Tassel Length: (from peduncle node to tassel tip), (cm). | 48.3 | 7.93 | 15 |
| Pollen Shed: 0 = male sterile, 9 = heavy shed | 6 | | |
| * Anther Color: Pale Yellow Munsell: 7.5Y86 | | | |
| * Glume Color: Purple Munsell: 10RP26 | | | |
| * Bar Glumes (glume bands): 1 = absent, 2 = present | 1 | | |
| Peduncle Length: (from top leaf node to lower florets or branches), (cm). | 20.5 | 0.92 | 15 |
| * Munsell Glossy Book of Color, (A standard color reference). Kollmorgen Inst. Corp. New Windsor, NY. | | | |

TABLE 1-continued

VARIETY DESCRIPTION INFORMATION
VARIETY = PH8JR

6a. EAR (Unhusked ear)
   * Silk color: Red Munsell: 2.5R38
     (3 days after silk emergence)
   * Fresh husk color: Med. Green Munsell: 5GY68
   * Dry husk color: White Munsell: 10YR92
     (65 days after 50% silking)

| | | | |
|---|---|---|---|
| Ear position at dry husk stage: 1 = upright, 2 = horizontal, 3 = pendant | 2 | | |
| Husk Tightness: (1 = very loose, 9 = very tight) | 5 | | |
| Husk Extension (at harvest): 1 = short(ears exposed), 2 = medium (<8 cm), 3 = long (8–10 cm), 4 = v. long (>10 cm) | 2 | | |

6b. EAR (Husked ear data)

| | | | |
|---|---|---|---|
| Ear Length (cm): | 13.1 | 0.70 | 15 |
| Ear Diameter at mid-point (mm) | 42.8 | 1.97 | 15 |
| Ear Weight (gm): | 104.7 | 17.37 | 15 |
| Number of Kernel Rows: | 15.1 | 1.49 | 15 |
| Kernel Rows: 1 = indistinct, 2 = distinct | 2 | | |
| Row Alignment: 1 = straight, 2 = slightly curved, 3 = spiral | 2 | | |
| Shank Length (cm): | 11.6 | 2.59 | 15 |
| Ear Taper: 1 = slight cylind., 2 = average, 3 = extreme | 2 | | |

7. KERNEL (Dried):

| | | | |
|---|---|---|---|
| Kernel Length (mm): | 10.7 | 0.62 | 15 |
| Kernel Width (mm): | 8.6 | 0.63 | 15 |
| Kernel Thickness (mm): | 5.1 | 0.80 | 15 |
| Round Kernels (shape grade) (%) | 47.5 | 4.54 | 3 |
| Aleurone Color Pattern: 1 = homozygous, 2 = segregating | 1 | | |

* Aleurone Color: Yellow Munsell: 10YR814
   * Hard Endo. Color: Yellow Munsell: 10YR714

| | | | |
|---|---|---|---|
| Endosperm Type: 1 = sweet (su1), 2 = extra sweet (sh2), 3 = normal starch, 4 = high amylose starch, 5 = waxy starch, 6 = high protein, 7 = high lysine, 8 = super sweet (se), 9 = high oil, 10 = other | 3 | | |
| Weight per 100 Kernels (unsized sample) (gm): | 28.0 | 1.73 | 3 |

8. COB:
   * Cob Diameter at mid-point (mm): 25.1   1.25   15
   * Cob Color: Pink Munsell: 10R66
   * Munsell Glossy Book of color, (A standard color reference). Kollmorgen Inst. Corp. New Windsor, NY.

10. DISEASE RESISTANCE:
    (Rate from 1 = most-susceptable to 9 = most-resistant. Leave blank if not tested, leave race or strain options blank if polygenic.)

A. LEAF BLIGHTS, WILTS, AND LOCAL INFECTION DISEASES
        Anthracnose Leaf Blight (*Colletotrichum graminicola*)
        Common Rust (*Puccinia sorghi*)
        Common Smut (*Ustilago maydis*)
      6 Eyespot (*Kabatiella zeae*)
      7 Gross's Wilt (*Clavibacter michiganense* spp. *nebraskense*)
      3 Gray Leaf Spot (*Cercospora zeae-maydis*)
        Helminthosporium Leaf Spot (*Bipolaris zeicola*) Race:
      5 Northern Leaf Blight (*Exserohilum turcicum*) Race:
        Southern Leaf Blight (*Bipolaris maydis*) Race:
      8 Southern Rust (*Puccinia polysora*)
        Stewart's Wilt (*Erwinia stewartii*)
        Other (Specify): _____

B. SYSTEMIC DISEASES
        Corn Lethal Necrosis (MCMV and MDMV)
      9 Head Smut (*Sphacelotheca reiliana*)
        Maize Chlorotic Dwarf Virus (MDV)
        Maize Chlorotic Mottle Virus (MCMV)
      5 Maize Dwarf Mosaic Virus (MDMV)
        Sorghum Downy Mildew of Corn (*Peronosclerospora sorghi*)
        Other (Specify): _____

C. STALK ROTS
      6 Anthracnose Stalk Rot (*Colletotrichum graminicola*)
        Diplodia Stalk Rot (*Stenocarpella maydis*)
        *Fusarium* Stalk Rot (*Fusarium moniliforme*)
        *Gibberella* Stalk Rot (*Gibberella zeae*)
        Other (Specify): _____

D. EAR AND KERNEL ROTS
        *Aspergillus* Ear and Kernel Rot (*Aspergillus flavus*)
      6 Diplodia Ear Rot (*Stenocarpella maydis*)
        *Fusarium* Ear and Kernel Rot (*Fusarium moniliforme*)
      6 Gibberella Ear Rot (*Gibberella zeae*)
        Other (Specify): _____

11. INSECT RESISTANCE:
    (Rate from 1 = most-suscept. to 9 = most-resist., leave blank if not tested.)

TABLE 1-continued

VARIETY DESCRIPTION INFORMATION
VARIETY = PH8JR

Corn Worm (*Helicoverpa zea*)
  __ Leaf Feeding
  __ Silk Feeding
  __ Ear Damage
Corn Leaf Aphid (*Rophalosiphum maydis*)
Corn Sap Beetle (*Capophilus dimidiatus*)
European Corn Borer (*Ostrinia nubilalis*)
  1st. Generation (Typically whorl leaf feeding)
  2nd. Generation (Typically leaf sheath-collar feeding)
  __ Stalk Tunneling
  __ cm tunneled/plant
Fall armyworm (*Spodoptera fruqiperda*)
  __ Leaf Feeding
  __ Silk Feeding
  __ mg larval wt.
Maize Weevil (*Sitophilus zeamaize*)
Northern Rootworm (*Diabrotica barberi*)
Southern Rootworm (*Diabrotica undecimpunctata*)
Southwestern Corn Borer (*Diatreaea grandiosella*)
  __ Leaf Feeding
  __ Stalk Tunneling
  __ cm tunneled/plant
Two-spotted Spider Mite (*Tetranychus utricae*)
Western Rootworm (*Diabrotica virgifrea virgifrea*)
Other (Specify): _____
12. AGRONOMIC TRAITS:
  Staygreen (at 65 days after anthesis; rate from 1-worst to 9-excellent)
  % Dropped Ears (at 65 days after anthesis)
  % Pre-anthesis Brittle Snapping
  % Pre-anthesis Root Lodging
  % Post-anthesis Root Lodging (at 65 days after anthesis)
  % Post-anthesis Stalk Lodging
6,027.0 Kg/ha (Yield at 12–13% grain moisture)

TABLE 2

SSR PROFILE OF PH8JR

| Bin # | Marker Name | Base Pairs |
|---|---|---|
| 1.01 | BNLG1014 | 124.07 |
| 1.01 | PHI056 | 249.16 |
| 1.01 | UMC1170 | 230.01 |
| 1.01 | UMC2215 | 143.34 |
| 1.01 | UMC2225 | 300.54 |
| 1.02 | BNLG1007 | 132.72 |
| 1.02 | BNLG1083 | 221.67 |
| 1.02 | BNLG1127 | 96.25 |
| 1.02 | BNLG1953 | 205.94 |
| 1.03 | BNGL439 | 231.84 |
| 1.03 | BNLG1203 | 306.41 |
| 1.03 | PHI109275 | 131.92 |
| 1.04 | BNLG2086 | 225.88 |
| 1.04 | BNLG2238 | 228.75 |
| 1.05 | BNLG1832 | 223.44 |
| 1.05 | BNLG1886 | 141.36 |
| 1.06 | BNLG1057 | 247.06 |
| 1.06 | BNLG1615 | 219.09 |
| 1.06 | UMC1035 | 292.64 |
| 1.07 | BNLG1556 | 207.57 |
| 1.09 | BNLG1331 | 146.26 |
| 1.09 | BNLG1720 | 236.71 |
| 1.09 | UMC1306 | 147.75 |
| 1.1 | PHI308707 | 131.29 |
| 1.11 | PHI064 | 80.52 |
| 1.11 | PHI227562 | 322.63 |
| 1.11 | PHI265454 | 217.51 |
| 1.11 | UMC1630 | 171.06 |
| 2 | UMC1419 | 110.04 |
| 2.01 | PHI96100 | 279.92 |
| 2.01 | UMC1227 | 139.44 |
| 2.01 | UMC1378 | 126.86 |
| 2.02 | UMC1265 | 293.86 |
| 2.03 | BNLG1064 | 187.89 |
| 2.03 | PHI109642 | 138.15 |
| 2.04 | PHI083 | 125.54 |
| 2.04 | UMC1326 | 139.68 |
| 2.05 | BNLG1909 | 297.35 |
| 2.05 | PHI014 | 431.86 |
| 2.05 | UMC1202 | 248.95 |
| 2.05 | UMC1275 | 305.59 |
| 2.05 | UMC1506 | 168.64 |
| 2.06 | BNLG1036 | 200.93 |
| 2.06 | BNLG1138 | 224.02 |
| 2.06 | BNLG1396 | 133.78 |
| 2.06 | BNLG1831 | 194.38 |
| 2.06 | UMC1299 | 143.45 |
| 2.07 | BNLG1927 | 198.49 |
| 2.07 | PHI251315 | 124.14 |
| 2.07 | UMC1560 | 136.43 |
| 2.08 | BNLG1141 | 152.76 |
| 2.08 | BNLG1258 | 217.59 |
| 2.08 | BNLG1940 | 245.96 |
| 2.08 | PHI435417 | 214.07 |
| 2.08 | UMC1049 | 134.37 |
| 2.08 | UMC1889 | 113.43 |
| 2.09 | BNLG1520 | 296.02 |
| 2.09 | UMC1736 | 280.81 |
| 3 | PHI453121 | 217.75 |
| 3.01 | PHI104127 | 169.3 |
| 3.01 | PHI404206 | 300.2 |
| 3.02 | BNLG1647 | 131.21 |
| 3.03 | BNLG1523 | 318.87 |
| 3.03 | UMC2053 | 103.67 |

TABLE 2-continued

SSR PROFILE OF PH8JR

| Bin # | Marker Name | Base Pairs |
|---|---|---|
| 3.04 | BNLG1452 | 84.3 |
| 3.04 | BNLG1638 | 225.53 |
| 3.04 | BNLG2241 | 142.55 |
| 3.04 | PHI029 | 150.78 |
| 3.04 | UMC1036 | 325.45 |
| 3.05 | BNLG1035 | 112.73 |
| 3.05 | PHI073 | 185.47 |
| 3.06 | BNLG1160 | 222.29 |
| 3.06 | BNLG1951 | 127.16 |
| 3.06 | PHI102228 | 135.65 |
| 3.1 | UMC1136 | 146.22 |
| 4 | PHI072 | 139.87 |
| 4.01 | PHI295450 | 185.19 |
| 4.05 | BNLG1159 | 147.98 |
| 4.05 | BNLG1265 | 233.6 |
| 4.05 | BNLG1755 | 214.75 |
| 4.05 | BNLG1937 | 237.9 |
| 4.05 | UMC1142 | 155.26 |
| 4.05 | UMC1175 | 139.5 |
| 4.05 | UMC1303 | 127.11 |
| 4.05 | UMC1317 | 113.98 |
| 4.05 | UMC1346 | 93.56 |
| 4.05 | UMC1382 | 159.82 |
| 4.05 | UMC1390 | 133.46 |
| 4.05 | UMC1451 | 114.16 |
| 4.05 | UMC1511 | 166.03 |
| 4.05 | UMC1548 | 159.65 |
| 4.05 | UMC1702 | 100.99 |
| 4.05 | UMC1791 | 157.13 |
| 4.05 | UMC1851 | 114.24 |
| 4.05 | UMC1896 | 87.94 |
| 4.05 | UMC1964 | 146.26 |
| 4.05 | UMC2054 | 151.03 |
| 4.05 | UMC2055 | 85.46 |
| 4.05 | UMC2061 | 125.27 |
| 4.06 | BNLG1621 | 171.17 |
| 4.06 | BNLG2291 | 160.75 |
| 4.06 | BNLG252 | 165.91 |
| 4.06 | MMC0371 | 266.96 |
| 4.06 | UMC1662 | 111.99 |
| 4.06 | UMC1869 | 154.5 |
| 4.06 | UMC1945 | 113.42 |
| 4.06 | UMC2027 | 116.74 |
| 4.07 | BNLG1784 | 231.42 |
| 4.07 | UMC1620 | 144.23 |
| 4.08 | DUPSSR28 | 128.38 |
| 4.08 | PHI093 | 280.62 |
| 4.08 | UMC1086 | 105.88 |
| 4.08 | UMC1371 | 163.14 |
| 4.08 | UMC1667 | 154.65 |
| 4.08 | UMC1808 | 139.76 |
| 4.08 | UMC1856 | 189.59 |
| 4.08 | UMC1871 | 128.64 |
| 4.08 | UMC1899 | 111.61 |
| 4.08 | UMC2041 | 171.36 |
| 4.08 | UMC2187 | 87.14 |
| 4.08 | UMC2188 | 167.98 |
| 4.09 | BNLG1565 | 204.75 |
| 4.09 | UMC1101 | 137.46 |
| 4.09 | UMC1173 | 159.94 |
| 4.09 | UMC1328 | 161.27 |
| 4.09 | UMC1559 | 141.08 |
| 4.09 | UMC1574 | 167.24 |
| 4.09 | UMC1631 | 139.84 |
| 4.09 | UMC1650 | 139.65 |
| 4.09 | UMC1820 | 138.88 |
| 4.09 | UMC1940 | 113.49 |
| 4.09 | UMC1999 | 110.95 |
| 4.09 | UMC2046 | 143.72 |
| 4.09 | UMC2139 | 133.81 |
| 4.11 | BNLG1890 | 265.49 |
| 4.11 | PHI076 | 170.15 |
| 5.01 | PHI024 | 367.71 |
| 5.03 | PHI109188 | 161.39 |
| 5.03 | UMC1352 | 148.67 |
| 5.04 | BNGL653 | 154.37 |
| 5.04 | BNLG1208 | 118.8 |
| 5.04 | BNLG2323 | 190.16 |
| 5.04 | BNLG653 | 155.49 |
| 5.04 | UMC1424 | 294.12 |
| 5.05 | PHI333597 | 210.64 |
| 5.05 | UMC2386 | 124.59 |
| 5.06 | PHI085 | 248.53 |
| 5.07 | BNLG1346 | 189.41 |
| 5.07 | BNLG1711 | 177.02 |
| 5.09 | BNLG386 | 141.62 |
| 6 | UMC1002 | 131.62 |
| 6 | UMC1143 | 226.51 |
| 6 | UMC1753 | 200.48 |
| 6 | UMC1883 | 84 |
| 6.01 | BNLG1422 | 216.01 |
| 6.01 | PHI077 | 124.85 |
| 6.01 | PHI159819 | 135.52 |
| 6.01 | UMC1133 | 219.92 |
| 6.01 | UMC1186 | 268.95 |
| 6.01 | UMC1195 | 134.57 |
| 6.01 | UMC1229 | 245.9 |
| 6.01 | UMC1498 | 117.97 |
| 6.01 | UMC1517 | 103.35 |
| 6.01 | UMC1596 | 103.2 |
| 6.01 | UMC2056 | 163.85 |
| 6.02 | UMC1006 | 198.72 |
| 6.02 | UMC1083 | 337.9 |
| 6.02 | UMC1572 | 201.7 |
| 6.02 | UMC1656 | 135.89 |
| 6.02 | UMC1818 | 113.43 |
| 6.04 | UMC1857 | 150.85 |
| 6.04 | UMC1918 | 167.38 |
| 6.04 | UMC2006 | 117.26 |
| 6.04 | UMC2317 | 129.64 |
| 6.05 | BNLG1174 | 218.98 |
| 6.05 | UMC1020 | 136.63 |
| 6.05 | UMC1045 | 179.04 |
| 6.05 | UMC1187 | 114.04 |
| 6.05 | UMC1250 | 270.12 |
| 6.05 | UMC1314 | 342.12 |
| 6.05 | UMC1341 | 351.4 |
| 6.05 | UMC1795 | 125.16 |
| 6.06 | UMC1474 | 220.97 |
| 6.06 | UMC1762 | 316.65 |
| 6.06 | UMC1859 | 93.02 |
| 6.06 | UMC1912 | 162.77 |
| 6.07 | PHI299852 | 117.34 |
| 6.07 | UMC1127 | 235.46 |
| 6.07 | UMC1248 | 122.27 |
| 6.07 | UMC1296 | 141.75 |
| 6.07 | UMC1621 | 211.45 |
| 6.07 | UMC1653 | 252.11 |
| 7 | BNLG2132 | 200.47 |
| 7 | UMC1241 | 120.99 |
| 7 | UMC1546 | 279.87 |
| 7 | UMC1642 | 149.49 |
| 7.01 | BNLG1292 | 121.56 |
| 7.01 | PHI057 | 409.17 |
| 7.01 | UMC1270 | 255.1 |
| 7.01 | UMC1632 | 150.12 |
| 7.02 | BNLG1094 | 145.01 |
| 7.02 | DUPSSR9 | 103.58 |
| 7.02 | PHI034 | 137.99 |
| 7.02 | UMC1138 | 255.74 |
| 7.02 | UMC1393 | 323.32 |
| 7.02 | UMC1401 | 165.83 |
| 7.02 | UMC1433 | 135.24 |
| 7.02 | UMC1929 | 160.35 |
| 7.02 | UMC1978 | 115.21 |
| 7.02 | UMC2327 | 134.59 |
| 7.03 | BNLG1070 | 161.18 |
| 7.03 | BNLG155 | 221.61 |
| 7.03 | BNLG2271 | 233.78 |
| 7.03 | UMC1015 | 119.92 |

TABLE 2-continued

SSR PROFILE OF PH8JR

| Bin # | Marker Name | Base Pairs |
|---|---|---|
| 7.03 | UMC1112 | 254.1 |
| 7.03 | UMC1134 | 320.91 |
| 7.03 | UMC1301 | 335.08 |
| 7.03 | UMC1324 | 214.86 |
| 7.03 | UMC1450 | 126.89 |
| 7.03 | UMC1456 | 120.13 |
| 7.03 | UMC1567 | 312.76 |
| 7.03 | UMC1660 | 204.63 |
| 7.03 | UMC1713 | 139.56 |
| 7.03 | UMC1865 | 145.03 |
| 7.03 | UMC1888 | 145.88 |
| 7.04 | PHI328175 | 123.14 |
| 7.04 | UMC1125 | 190.23 |
| 7.04 | UMC1295 | 247.91 |
| 7.04 | UMC1412 | 157.09 |
| 7.04 | UMC1710 | 235.34 |
| 7.04 | UMC1768 | 148.95 |
| 7.04 | UMC1782 | 321.51 |
| 7.04 | UMC1799 | 104.77 |
| 7.04 | UMC1944 | 147.62 |
| 7.05 | PHI069 | 201.25 |
| 7.05 | UMC1154 | 280.72 |
| 7.05 | UMC1407 | 359.56 |
| 7.05 | UMC1760 | 235.85 |
| 7.05 | UMC2059 | 127.35 |
| 7.06 | PHI116 | 164.96 |
| 7.06 | UMC1740 | 98.25 |
| 8.01 | UMC1139 | 305.98 |
| 8.01 | UMC1483 | 310.46 |
| 8.01 | UMC1786 | 332.37 |
| 8.01 | UMC2042 | 107.84 |
| 8.02 | UMC1034 | 130.73 |
| 8.02 | UMC1304 | 251.57 |
| 8.02 | UMC1428 | 321.5 |
| 8.02 | UMC1790 | 157.73 |
| 8.02 | UMC1872 | 152.85 |
| 8.02 | UMC1913 | 162.08 |
| 8.02 | UMC1974 | 485.86 |
| 8.02 | UMC2004 | 97.74 |
| 8.03 | BNLG1863 | 244.62 |
| 8.03 | PHI100175 | 143.86 |
| 8.03 | PHI121 | 97.85 |
| 8.03 | UMC1157 | 209.86 |
| 8.03 | UMC1289 | 221.6 |
| 8.03 | UMC1457 | 341.28 |
| 8.03 | UMC1470 | 337.13 |
| 8.03 | UMC1735 | 95.22 |
| 8.03 | UMC1741 | 162.93 |
| 8.03 | UMC1807 | 104.29 |
| 8.03 | UMC1904 | 155.26 |
| 8.03 | UMC1910 | 170.94 |
| 8.03 | UMC2057 | 151.58 |
| 8.04 | BNLG2046 | 320.6 |
| 8.04 | UMC1172 | 338.31 |
| 8.04 | UMC1343 | 323.1 |
| 8.04 | UMC1858 | 128.13 |
| 8.05 | BNLG1176 | 218.27 |
| 8.05 | UMC1130 | 236.59 |
| 8.05 | UMC1141 | 306.74 |
| 8.05 | UMC1263 | 348.29 |
| 8.05 | UMC1287 | 306.43 |
| 8.05 | UMC1316 | 233.27 |
| 8.05 | UMC1562 | 210.13 |
| 8.05 | UMC1777 | 119.15 |
| 8.05 | UMC1864 | 170.73 |
| 8.05 | UMC1882 | 114.55 |
| 8.05 | UMC1959 | 330.12 |
| 8.06 | BNLG1031 | 288.1 |
| 8.06 | UMC1149 | 216.49 |
| 8.06 | UMC1161 | 258.12 |
| 8.06 | UMC1670 | 124.54 |
| 8.07 | BNLG1065 | 215.75 |
| 8.07 | BNLG1828 | 185.67 |
| 8.07 | UMC1607 | 214.4 |
| 8.08 | BNLG1056 | 110.55 |
| 8.08 | PHI015 | 93.67 |
| 8.08 | UMC2052 | 146.33 |
| 8.09 | PHI233376 | 135.73 |
| 8.09 | UMC1638 | 147.71 |
| 9 | UMC2393 | 206.53 |
| 9.01 | BNLG1810 | 211.1 |
| 9.01 | BNLG2122 | 235.19 |
| 9.01 | PHI033 | 248.95 |
| 9.01 | UMC1588 | 316.93 |
| 9.01 | UMC1958 | 231.65 |
| 9.02 | UMC1131 | 362.35 |
| 9.02 | UMC1764 | 304.74 |
| 9.02 | UMC2213 | 106.3 |
| 9.02 | UMC2219 | 254.22 |
| 9.02 | UMC2336 | 262.53 |
| 9.03 | BNLG1217 | 210.36 |
| 9.03 | GL15 | 161.42 |
| 9.03 | PHI079 | 185.78 |
| 9.03 | UMC1267 | 338.24 |
| 9.03 | UMC1336 | 309.96 |
| 9.03 | UMC1377 | 216.01 |
| 9.03 | UMC1420 | 313.52 |
| 9.03 | UMC1614 | 332.98 |
| 9.03 | UMC1743 | 136.79 |
| 9.03 | UMC2087 | 266.34 |
| 9.03 | UMC2394 | 363.42 |
| 9.04 | BNLG1012 | 157.34 |
| 9.04 | MMP96 | 220.74 |
| 9.04 | UMC1522 | 252.96 |
| 9.04 | UMC1771 | 330.87 |
| 9.04 | UMC2121 | 164.5 |
| 9.04 | UMC2398 | 126.25 |
| 9.05 | MMP179 | 161.37 |
| 9.05 | UMC1078 | 353.33 |
| 9.05 | UMC1357 | 254.49 |
| 9.05 | UMC1417 | 209.65 |
| 9.05 | UMC1519 | 252.58 |
| 9.05 | UMC1794 | 115.4 |
| 9.05 | UMC1805 | 146.58 |
| 9.05 | UMC2341 | 122.07 |
| 9.06 | PHI448880 | 183.67 |
| 9.06 | UMC2346 | 300.4 |
| 9.07 | BNGL619 | 273.05 |
| 9.07 | UMC1714 | 161.49 |
| 9.07 | UMC2089 | 134.52 |
| 9.07 | UMC2131 | 264.31 |
| 9.08 | BNLG1129 | 300.74 |
| 9.08 | UMC1505 | 142.16 |
| 10 | PHI041 | 216.82 |
| 10 | UMC1293 | 158.43 |
| 10.01 | UMC1318 | 219.59 |
| 10.01 | UMC2018 | 154.72 |
| 10.02 | BNLG1429 | 190.4 |
| 10.02 | PHI059 | 153.21 |
| 10.02 | UMC1337 | 311.63 |
| 10.02 | UMC1432 | 119.15 |
| 10.02 | UMC1576 | 151.27 |
| 10.02 | UMC2034 | 132.92 |
| 10.02 | UMC2069 | 375.28 |
| 10.03 | BNLG1079 | 170.4 |
| 10.03 | UMC1037 | 244.94 |
| 10.03 | UMC1312 | 315.7 |
| 10.03 | UMC1345 | 166.56 |
| 10.03 | UMC1367 | 327.38 |
| 10.03 | UMC1381 | 210.29 |
| 10.03 | UMC1666 | 151.46 |
| 10.03 | UMC1739 | 317.36 |
| 10.03 | UMC1863 | 161.75 |
| 10.03 | UMC1866 | 164.06 |
| 10.03 | UMC1962 | 126.3 |
| 10.03 | UMC2016 | 129.4 |
| 10.03 | UMC2067 | 165.4 |
| 10.04 | PHI062 | 161.19 |
| 10.04 | UMC1054 | 348.35 |
| 10.04 | UMC1246 | 230.53 |

TABLE 2-continued

SSR PROFILE OF PH8JR

| Bin # | Marker Name | Base Pairs |
|---|---|---|
| 10.04 | UMC1272 | 201.73 |
| 10.04 | UMC1280 | 308.71 |
| 10.04 | UMC1330 | 340.53 |
| 10.04 | UMC1487 | 338.8 |
| 10.04 | UMC1507 | 319.26 |
| 10.04 | UMC1648 | 141.55 |
| 10.04 | UMC1930 | 106.79 |
| 10.04 | UMC2003 | 89.1 |
| 10.05 | BNLG1074 | 161.84 |
| 10.06 | UMC1249 | 233.74 |
| 10.07 | BNLG1450 | 190.02 |
| 10.07 | BNLG1839 | 187.07 |
| 10.07 | UMC1084 | 221.96 |
| 10.07 | UMC1176 | 339.25 |
| 10.07 | UMC1640 | 107.9 |
| 10.07 | UMC1645 | 158.73 |
| 10.07 | UMC2021 | 135.41 |

TABLE 3A

PAIRED INBRED COMPARISON REPORT
Variety #1: PH8JR
Variety #2: PH1B8

| Stat | YIELD BU/A 56# ABS | YIELD BU/A 56# % MN | MST PCT ABS | EGRWTH SCORE ABS | ESTCNT COUNT ABS | TILLER PCT ABS |
|---|---|---|---|---|---|---|
| Mean1 | 125.6 | 106.9 | 17.3 | 5.7 | 27.6 | 1.1 |
| Mean2 | 115.4 | 98.1 | 20.0 | 5.3 | 21.9 | 2.2 |
| Locs | 8 | 8 | 8 | 15 | 24 | 16 |
| Reps | 16 | 16 | 16 | 15 | 25 | 16 |
| Diff | 10.2 | 8.8 | 2.7 | 0.4 | 5.7 | 1.1 |
| Prob | 0.024 | 0.028 | 0.001 | 0.054 | 0.000 | 0.293 |

| Stat | GDUSHD GDU ABS | GDUSLK GDU ABS | POLWT VALUE ABS | POLWT VALUE % MN | TASBLS SCORE ABS | TASSZ SCORE ABS |
|---|---|---|---|---|---|---|
| Mean1 | 132.5 | 133.7 | 140.0 | 103.6 | 9.0 | 5.3 |
| Mean2 | 137.8 | 139.1 | 162.5 | 128.2 | 9.0 | 6.0 |
| Locs | 56 | 57 | 7 | 7 | 2 | 49 |
| Reps | 56 | 58 | 14 | 14 | 2 | 49 |
| Diff | −5.3 | −5.4 | −22.4 | −24.6 | 0.0 | −0.7 |
| Prob | 0.000 | 0.000 | 0.560 | 0.352 | 1.000 | 0.000 |

| Stat | PLTHT CM ABS | EARHT CM ABS | STAGRN SCORE ABS | STKLDG % NOT ABS | SCTGRN SCORE ABS | TEXEAR SCORE ABS |
|---|---|---|---|---|---|---|
| Mean1 | 182.8 | 76.0 | 3.3 | 95.2 | 8.3 | 5.0 |
| Mean2 | 187.7 | 80.0 | 5.7 | 100.0 | 7.4 | 7.0 |
| Locs | 41 | 7 | 15 | 1 | 10 | 1 |
| Reps | 41 | 7 | 15 | 1 | 10 | 1 |
| Diff | −5.0 | −4.0 | −2.4 | −4.8 | 0.9 | −2.0 |
| Prob | 0.016 | 0.488 | 0.000 | — | 0.121 | — |

| Stat | EARMLD SCORE ABS | BARPLT % NOT ABS | GLFSPT SCORE ABS | NLFBLT SCORE ABS | STWWLT SCORE ABS | ANTROT SCORE ABS |
|---|---|---|---|---|---|---|
| Mean1 | 7.6 | 98.1 | 3.2 | 5.7 | 7.0 | 5.0 |
| Mean2 | 7.6 | 97.2 | 3.8 | 5.5 | 7.0 | 5.8 |
| Locs | 5 | 24 | 8 | 3 | 1 | 2 |
| Reps | 5 | 24 | 11 | 5 | 1 | 4 |
| Diff | 0.0 | 0.9 | −0.6 | 0.2 | 0.0 | −0.8 |
| Prob | 1.000 | 0.431 | 0.366 | 0.742 | — | 0.795 |

| Stat | FUSERS SCORE ABS | DIPERS SCORE ABS | EYESPT SCORE ABS | COMRST SCORE ABS | HC BLT SCORE ABS | ECBDPE % NOT ABS |
|---|---|---|---|---|---|---|
| Mean1 | 5.5 | 5.5 | 6.0 | 6.0 | 8.0 | 97.0 |
| Mean2 | 6.5 | 6.0 | 5.5 | 6.3 | 8.0 | 100.0 |
| Locs | 7 | 1 | 1 | 4 | 1 | 1 |
| Reps | 9 | 1 | 2 | 4 | 2 | 2 |
| Diff | −1.0 | −0.5 | 0.5 | −0.3 | 0.0 | −3.0 |
| Prob | 0.172 | — | — | 0.638 | — | — |

TABLE 3A-continued

PAIRED INBRED COMPARISON REPORT
Variety #1: PH8JR
Variety #2: PH1B8

| Stat | CLDTST PCT ABS | CLDTST PCT % MN | KSZDCD PCT ABS | HD SMT % NOT ABS | ERTLDG % NOT ABS | ERTLPN % NOT ABS | LRTLPN % NOT ABS |
|---|---|---|---|---|---|---|---|
| Mean1 | 92.0 | 101.7 | 5.6 | 95.8 | 100.0 | 100.0 | 96.3 |
| Mean2 | 94.8 | 104.9 | 4.8 | 100.0 | 100.0 | 100.0 | 93.8 |
| Locs | 11 | 11 | 11 | 1 | 1 | 2 | 2 |
| Reps | 11 | 11 | 11 | 1 | 1 | 2 | 3 |
| Diff | −2.8 | −3.2 | 0.8 | −4.2 | 0.0 | 0.0 | 2.5 |
| Prob | 0.080 | 0.078 | 0.311 | — | — | 1.000 | 0.500 |

TABLE 3B

PAIRED INBRED COMPARISON REPORT
Variety #1: PH8JR
Variety #2: PH24E

| Stat | YIELD BU/A 56# ABS | YIELD BU/A 56# % MN | MST PCT ABS | TSTWT LB/BU ABS | EGRWTH SCORE ABS | ESTCNT COUNT ABS |
|---|---|---|---|---|---|---|
| Mean1 | 83.8 | 110.6 | 18.4 | 54.1 | 5.6 | 26.8 |
| Mean2 | 93.0 | 125.6 | 27.3 | 54.0 | 5.1 | 24.9 |
| Locs | 19 | 19 | 21 | 6 | 26 | 35 |
| Reps | 27 | 27 | 29 | 8 | 26 | 36 |
| Diff | −9.2 | −15.0 | 9.0 | 0.2 | 0.5 | 1.9 |
| Prob | 0.044 | 0.010 | 0.124 | 0.769 | 0.013 | 0.000 |

| Stat | TILLER PCT ABS | GDUSHD GDU ABS | GDUSLK GDU ABS | POLWT VALUE ABS | POLWT VALUE % MN | TASBLS SCORE ABS |
|---|---|---|---|---|---|---|
| Mean1 | 1.0 | 132.1 | 133.4 | 175.1 | 102.6 | 8.3 |
| Mean2 | 0.9 | 135.5 | 139.4 | 132.2 | 80.3 | 7.7 |
| Locs | 21 | 96 | 97 | 7 | 7 | 3 |
| Reps | 21 | 96 | 98 | 14 | 14 | 3 |
| Diff | −0.1 | −3.3 | −6.0 | 42.9 | 22.3 | 0.7 |
| Prob | 0.798 | 0.000 | 0.000 | 0.041 | 0.020 | 0.423 |

| Stat | TASSZ SCORE ABS | PLTHT CM ABS | EARHT CM ABS | STAGRN SCORE ABS | STKLDG % NOT ABS | BRTSTK % NOT ABS |
|---|---|---|---|---|---|---|
| Mean1 | 5.4 | 182.2 | 76.5 | 3.6 | 97.6 | 99.1 |
| Mean2 | 5.3 | 199.8 | 86.5 | 6.5 | 100.0 | 97.7 |
| Locs | 81 | 69 | 15 | 22 | 2 | 4 |
| Reps | 81 | 69 | 15 | 22 | 2 | 5 |
| Diff | 0.1 | −17.6 | −9.9 | −2.9 | −2.4 | 1.4 |
| Prob | 0.364 | 0.000 | 0.008 | 0.000 | 0.500 | 0.388 |

| Stat | SCTGRN SCORE ABS | TEXEAR SCORE ABS | EARMLD SCORE ABS | BARPLT % NOT ABS | DRPEAR % NOT ABS | GLFSPT SCORE ABS |
|---|---|---|---|---|---|---|
| Mean1 | 8.0 | 6.0 | 7.1 | 98.4 | 100.0 | 3.0 |
| Mean2 | 7.1 | 6.5 | 7.0 | 98.4 | 100.0 | 4.6 |
| Locs | 14 | 2 | 8 | 40 | 1 | 10 |
| Reps | 14 | 2 | 8 | 41 | 1 | 16 |
| Diff | 0.9 | −0.5 | 0.1 | 0.0 | 0.0 | −1.5 |
| Prob | 0.068 | 0.795 | 0.732 | 0.993 | — | 0.044 |

| Stat | NLFBLT SCORE ABS | STWWLT SCORE ABS | ANTROT SCORE ABS | FUSERS SCORE ABS | GIBERS SCORE ABS | DIPERS SCORE ABS |
|---|---|---|---|---|---|---|
| Mean1 | 5.4 | 7.0 | 5.0 | 5.2 | 9.0 | 5.5 |
| Mean2 | 6.6 | 7.0 | 6.3 | 4.4 | 9.0 | 4.5 |
| Locs | 4 | 3 | 3 | 8 | 1 | 1 |
| Reps | 7 | 3 | 6 | 12 | 2 | 2 |

TABLE 3B-continued

PAIRED INBRED COMPARISON REPORT
Variety #1: PH8JR
Variety #2: PH24E

| Stat | | | | | | |
|---|---|---|---|---|---|---|
| Diff | −1.3 | 0.0 | −1.3 | 0.8 | 0.0 | 1.0 |
| Prob | 0.063 | 1.000 | 0.607 | 0.149 | — | — |

| Stat | EYESPT SCORE ABS | COMRST SCORE ABS | HC BLT SCORE ABS | ECBDPE % NOT ABS | CLDTST PCT ABS | CLDTST PCT % MN |
|---|---|---|---|---|---|---|
| Mean1 | 6.0 | 5.8 | 8.0 | 97.0 | 86.5 | 95.1 |
| Mean2 | 6.0 | 6.5 | 8.0 | 98.5 | 83.6 | 91.6 |
| Locs | 1 | 7 | 1 | 1 | 8 | 8 |
| Reps | 2 | 8 | 2 | 2 | 8 | 8 |
| Diff | 0.0 | −0.7 | 0.0 | −1.5 | 2.9 | 3.5 |
| Prob | — | 0.140 | — | — | 0.319 | 0.311 |

| Stat | KSZDCD PCT ABS | HD SMT % NOT ABS | ERTLDG % NOT ABS | LRTLDG % NOT ABS | ERTLPN % NOT ABS | LRTLPN % NOT ABS | STLLPN % NOT ABS |
|---|---|---|---|---|---|---|---|
| Mean1 | 6.4 | 95.8 | 97.0 | 100.0 | 100.0 | 96.3 | 63.0 |
| Mean2 | 7.3 | 54.5 | 83.0 | 100.0 | 99.8 | 85.0 | 96.3 |
| Locs | 9 | 1 | 3 | 1 | 4 | 2 | 1 |
| Reps | 9 | 2 | 3 | 1 | 4 | 3 | 1 |
| Diff | −1.0 | 41.3 | 14.0 | 0.0 | 0.3 | 11.3 | −33.3 |
| Prob | 0.304 | — | 0.200 | — | 0.391 | 0.500 | — |

TABLE 3C

PAIRED INBRED COMPARISON REPORT
Variety #1: PH8JR
Variety #2: PH7CP

| Stat | YIELD BU/A 56# ABS | YIELD BU/A 56# % MN | MST PCT ABS | TSTWT LB/BU ABS | EGRWTH SCORE ABS | ESTCNT COUNT ABS |
|---|---|---|---|---|---|---|
| Mean1 | 107.5 | 107.3 | 20.2 | 56.3 | 5.6 | 26.3 |
| Mean2 | 99.8 | 100.4 | 20.1 | 58.3 | 5.0 | 25.8 |
| Locs | 13 | 13 | 13 | 2 | 26 | 34 |
| Reps | 25 | 25 | 25 | 4 | 26 | 35 |
| Diff | 7.6 | 6.9 | −0.1 | −2.0 | 0.6 | 0.6 |
| Prob | 0.111 | 0.139 | 0.850 | 0.110 | 0.003 | 0.154 |

| Stat | TILLER PCT ABS | GDUSHD GDU ABS | GDUSLK GDU ABS | POLWT VALUE ABS | POLWT VALUE % MN | TASBLS SCORE ABS |
|---|---|---|---|---|---|---|
| Mean1 | 0.9 | 132.0 | 133.3 | 141.9 | 102.6 | 8.6 |
| Mean2 | 1.4 | 131.0 | 133.0 | 101.2 | 73.9 | 8.4 |
| Locs | 23 | 96 | 96 | 11 | 11 | 5 |
| Reps | 23 | 96 | 96 | 22 | 22 | 5 |
| Diff | 0.5 | 1.0 | 0.3 | 40.7 | 28.7 | 0.2 |
| Prob | 0.555 | 0.024 | 0.506 | 0.048 | 0.039 | 0.374 |

| Stat | TASSZ SCORE ABS | PLTHT CM ABS | EARHT CM ABS | STAGRN SCORE ABS | STKLDG % NOT ABS | BRTSTK % NOT ABS |
|---|---|---|---|---|---|---|
| Mean1 | 5.5 | 181.7 | 78.2 | 3.8 | 97.6 | 99.0 |
| Mean2 | 5.6 | 200.9 | 88.7 | 6.3 | 100.0 | 100.0 |
| Locs | 81 | 68 | 17 | 19 | 2 | 2 |
| Reps | 81 | 68 | 17 | 19 | 2 | 3 |
| Diff | −0.1 | −19.2 | −10.5 | −2.5 | −2.4 | −1.0 |
| Prob | 0.212 | 0.000 | 0.002 | 0.000 | 0.500 | 0.500 |

| Stat | SCTGRN SCORE ABS | TEXEAR SCORE ABS | EARMLD SCORE ABS | BARPLT % NOT ABS | GLFSPT SCORE ABS | STWWLT SCORE ABS |
|---|---|---|---|---|---|---|
| Mean1 | 8.2 | 5.0 | 7.0 | 98.4 | 3.5 | 7.0 |
| Mean2 | 7.3 | 5.0 | 5.4 | 98.3 | 5.3 | 7.0 |
| Locs | 13 | 1 | 7 | 37 | 4 | 2 |

TABLE 3C-continued

PAIRED INBRED COMPARISON REPORT
Variety #1: PH8JR
Variety #2: PH7CP

| | | | | | | |
|---|---|---|---|---|---|---|
| Reps | 13 | 1 | 7 | 37 | 4 | 2 |
| Diff | 0.8 | 0.0 | 1.6 | 0.1 | −1.8 | 0.0 |
| Prob | 0.021 | — | 0.072 | 0.859 | 0.235 | 1.000 |

| Stat | FUSERS SCORE ABS | COMRST SCORE ABS | ECBDPE % NOT ABS | CLDTST PCT ABS | CLDTST PCT % MN | KSZDCD PCT ABS |
|---|---|---|---|---|---|---|
| Mean1 | 7.4 | 6.8 | 97.0 | 94.6 | 100.4 | 5.6 |
| Mean2 | 4.8 | 7.0 | 92.4 | 96.4 | 102.3 | 7.6 |
| Locs | 5 | 4 | 1 | 8 | 8 | 9 |
| Reps | 5 | 4 | 2 | 8 | 8 | 9 |
| Diff | 2.6 | −0.3 | 4.5 | −1.8 | −1.9 | −2.0 |
| Prob | 0.012 | 0.718 | — | 0.139 | 0.133 | 0.055 |

| Stat | ERTLDG % NOT ABS | ERTLPN % NOT ABS | LRTLPN % NOT ABS |
|---|---|---|---|
| Mean1 | 94.4 | 100.0 | 100.0 |
| Mean2 | 82.4 | 100.0 | 100.0 |
| Locs | 1 | 5 | 2 |
| Reps | 1 | 5 | 2 |
| Diff | 12.1 | 0.0 | 0.0 |
| Prob | — | 1.000 | 1.000 |

TABLE 4

GENERAL COMBINING ABILITY REPORT
PH8JR

| | | |
|---|---|---|
| PRM Day ABS | Mean | 102 |
| PRM Day ABS | Reps | 4548 |
| PRMSHD Day ABS | Mean | 103 |
| PRMSHD Day ABS | Reps | 3856 |
| YIELD bu/a 56# ABS | Mean | 184.1 |
| YIELD bu/a 56# ABS | Reps | 2521 |
| YIELD bu/a 56# ABS | Years | 3 |
| YIELD bu/a 56# % MN | Mean | 101.3 |
| YIELD bu/a 56# % MN | Reps | 2521 |
| MST pct ABS | Mean | 19.8 |
| MST pct ABS | Reps | 2544 |
| MST pct % MN | Mean | 95.7 |
| MST pct % MN | Reps | 2544 |
| STLPCN % NOT % MN | Mean | 99 |
| STLPCN % NOT % MN | Reps | 497 |
| STLLPN % NOT % MN | Mean | 104 |
| STLLPN % NOT % MN | Reps | 896 |
| ERTLPN % NOT % MN | Mean | 109 |
| ERTLPN % NOT % MN | Reps | 112 |
| LRTLPN % NOT % MN | Mean | 108 |
| LRTLPN % NOT % MN | Reps | 201 |
| TSTWT lb/bu % MN | Mean | 99.8 |
| TSTWT lb/bu % MN | Reps | 1647 |
| STKCNT count % MN | Mean | 100 |
| STKCNT count % MN | Reps | 4138 |
| PLTHT in % MN | Mean | 98 |
| PLTHT in % MN | Reps | 775 |
| EARHT in % MN | Mean | 99 |
| EARHT in % MN | Reps | 761 |
| BRTSTK % NOT % MN | Mean | 101 |
| BRTSTK % NOT % MN | Reps | 431 |
| GLFSPT score ABS | Mean | 3 |
| GLFSPT score ABS | Reps | 170 |
| STAGRN score ABS | Mean | 5 |
| STAGRN score ABS | Reps | 576 |
| HSKCVR score ABS | Mean | 5 |
| HSKCVR score ABS | Reps | 10 |

TABLE 5A

HYBRID COMPARISON
INBREDS IN HYBRID COMBINATION REPORT
Variety #1: HYBRID CONTAINING PH8JR
Variety #2: 35Y54

| Stat | YIELD BU/A 56# ABS | YIELD BU/A 56# % MN | MST PCT % MN | EGRWTH SCORE % MN | ESTCNT COUNT % MN | GDUSHD GDU % MN |
|---|---|---|---|---|---|---|
| Mean1 | 185.6 | 103.7 | 96.5 | 91.5 | 102.8 | 101.8 |
| Mean2 | 180.8 | 101.1 | 103.6 | 76.5 | 98.8 | 100.7 |
| Locs | 131 | 131 | 132 | 14 | 5 | 34 |
| Reps | 142 | 142 | 145 | 14 | 7 | 41 |
| Diff | 4.8 | 2.6 | 7.0 | 15.0 | 4.1 | 1.1 |
| Prob | 0.008 | 0.011 | 0.000 | 0.011 | 0.444 | 0.001 |

TABLE 5A-continued

HYBRID COMPARISON
INBREDS IN HYBRID COMBINATION REPORT
Variety #1: HYBRID CONTAINING PH8JR
Variety #2: 35Y54

| Stat | GDUSLK GDU % MN | STKCNT COUNT % MN | PLTHT CM % MN | EARHT CM % MN | STAGRN SCORE % MN | STKLDG % NOT % MN |
|---|---|---|---|---|---|---|
| Mean1 | 101.7 | 99.3 | 103.3 | 106.7 | 98.9 | 101.3 |
| Mean2 | 101.2 | 99.8 | 99.2 | 96.1 | 118.4 | 101.3 |
| Locs | 29 | 215 | 35 | 33 | 44 | 1 |
| Reps | 36 | 313 | 45 | 40 | 49 | 2 |
| Diff | 0.5 | −0.6 | 4.1 | 10.6 | −19.5 | 0.0 |
| Prob | 0.299 | 0.149 | 0.000 | 0.000 | 0.001 | — |

| Stat | ABTSTK % NOT % MN | DRPEAR % NOT % MN | TSTWT LB/BU ABS | GLFSPT SCORE ABS | NLFBLT SCORE ABS | GOSWLT SCORE ABS |
|---|---|---|---|---|---|---|
| Mean1 | 68.7 | 99.9 | 55.0 | 3.8 | 5.3 | 8.0 |
| Mean2 | 111.7 | 100.4 | 54.0 | 5.1 | 7.2 | 7.5 |
| Locs | 3 | 3 | 76 | 5 | 11 | 1 |
| Reps | 18 | 3 | 78 | 7 | 17 | 2 |
| Diff | −43.0 | −0.5 | 1.0 | −1.3 | −1.9 | 0.5 |
| Prob | 0.057 | 0.462 | 0.000 | 0.137 | 0.000 | — |

| Stat | ANTROT SCORE ABS | FUSERS SCORE ABS | GIBERS SCORE ABS | EYESPT SCORE ABS | ECBDPE % NOT ABS | ECB1LF SCORE ABS |
|---|---|---|---|---|---|---|
| Mean1 | 4.5 | 5.1 | 7.3 | 4.0 | 97.5 | 3.3 |
| Mean2 | 5.3 | 5.3 | 6.0 | 5.5 | 99.4 | 3.3 |
| Locs | 4 | 7 | 4 | 1 | 10 | 1 |
| Reps | 8 | 11 | 6 | 2 | 12 | 3 |
| Diff | −0.8 | −0.2 | 1.3 | −1.5 | −1.9 | 0.0 |
| Prob | 0.014 | 0.407 | 0.014 | — | 0.012 | — |

| Stat | ECB2SC SCORE ABS | HSKCVR SCORE ABS | GIBROT SCORE ABS | DIPROT SCORE ABS | BRTSTK % NOT ABS | HD SMT % NOT ABS |
|---|---|---|---|---|---|---|
| Mean1 | 5.0 | 4.0 | 4.1 | 3.5 | 95.9 | 99.5 |
| Mean2 | 5.0 | 6.5 | 3.2 | 4.5 | 95.4 | 97.8 |
| Locs | 9 | 4 | 7 | 1 | 8 | 6 |
| Reps | 13 | 4 | 14 | 2 | 10 | 8 |
| Diff | 0.0 | −2.5 | 0.9 | −1.0 | 0.5 | 1.7 |
| Prob | 0.928 | 0.031 | 0.395 | — | 0.825 | 0.256 |

| Stat | ERTLPN % NOT ABS | LRTLPN % NOT ABS |
|---|---|---|
| Mean1 | 83.6 | 86.5 |
| Mean2 | 67.8 | 76.0 |
| Locs | 12 | 13 |
| Reps | 14 | 16 |
| Diff | 15.8 | 10.5 |
| Prob | 0.069 | 0.154 |

TABLE 5B

INBREDS IN HYBRID COMBINATION REPORT
Variety #1: HYBRID CONTAINING PH8JR
Variety #2: 35P12

| Stat | YIELD BU/A 56# ABS | YIELD BU/A 56# % MN | MST PCT % MN | EGRWTH SCORE % MN | ESTCNT COUNT % MN | GDUSHD GDU % MN |
|---|---|---|---|---|---|---|
| Mean1 | 184.0 | 103.6 | 96.5 | 90.6 | 102.8 | 101.8 |
| Mean2 | 176.5 | 99.1 | 101.6 | 111.6 | 103.6 | 100.6 |
| Locs | 137 | 137 | 138 | 17 | 5 | 34 |
| Reps | 150 | 150 | 153 | 19 | 7 | 41 |

TABLE 5B-continued

INBREDS IN HYBRID COMBINATION REPORT
Variety #1: HYBRID CONTAINING PH8JR
Variety #2: 35P12

| Stat | | | | | | |
|---|---|---|---|---|---|---|
| Diff | 7.5 | 4.5 | 5.1 | −21.0 | −0.8 | 1.2 |
| Prob | 0.000 | 0.000 | 0.000 | 0.001 | 0.876 | 0.001 |

| Stat | GDUSLK GDU % MN | STKCNT COUNT % MN | PLTHT CM % MN | EARHT CM % MN | STAGRN SCORE % MN | STKLDG % NOT % MN |
|---|---|---|---|---|---|---|
| Mean1 | 101.7 | 99.3 | 103.3 | 106.7 | 100.9 | 101.3 |
| Mean2 | 100.7 | 101.0 | 99.3 | 101.5 | 112.4 | 101.3 |
| Locs | 29 | 223 | 35 | 33 | 46 | 1 |
| Reps | 36 | 325 | 45 | 40 | 51 | 2 |
| Diff | 1.0 | −1.7 | 4.0 | 5.2 | −11.5 | 0.0 |
| Prob | 0.016 | 0.000 | 0.000 | 0.000 | 0.043 | — |

| Stat | ABTSTK % NOT % MN | DRPEAR % NOT % MN | TSTWT LB/BU ABS | GLFSPT SCORE ABS | NLFBLT SCORE ABS | GOSWLT SCORE ABS |
|---|---|---|---|---|---|---|
| Mean1 | 68.7 | 99.9 | 54.9 | 3.8 | 5.3 | 8.0 |
| Mean2 | 99.2 | 100.9 | 54.8 | 4.5 | 6.1 | 7.5 |
| Locs | 3 | 3 | 80 | 5 | 11 | 1 |
| Reps | 18 | 3 | 84 | 7 | 17 | 2 |
| Diff | −30.5 | −1.0 | 0.1 | −0.7 | −0.8 | 0.5 |
| Prob | 0.166 | 0.186 | 0.514 | 0.025 | 0.043 | — |

| Stat | ANTROT SCORE ABS | FUSERS SCORE ABS | GIBERS SCORE ABS | EYESPT SCORE ABS | ECBDPE % NOT ABS | ECB1LF SCORE ABS |
|---|---|---|---|---|---|---|
| Mean1 | 5.0 | 5.1 | 7.3 | 4.0 | 97.5 | 3.3 |
| Mean2 | 4.8 | 6.0 | 6.0 | 4.0 | 99.0 | 3.7 |
| Locs | 3 | 7 | 4 | 1 | 10 | 1 |
| Reps | 6 | 11 | 6 | 2 | 12 | 3 |
| Diff | 0.2 | −0.9 | 1.3 | 0.0 | −1.6 | −0.3 |
| Prob | 0.885 | 0.059 | 0.129 | — | 0.072 | — |

| Stat | ECB2SC SCORE ABS | HSKCVR SCORE ABS | GIBROT SCORE ABS | DIPROT SCORE ABS | BRTSTK % NOT ABS | HD SMT % NOT ABS |
|---|---|---|---|---|---|---|
| Mean1 | 5.0 | 4.2 | 4.8 | 3.5 | 95.9 | 99.5 |
| Mean2 | 4.7 | 6.6 | 2.7 | 3.5 | 96.5 | 98.7 |
| Locs | 9 | 5 | 8 | 1 | 8 | 6 |
| Reps | 13 | 6 | 15 | 2 | 10 | 8 |
| Diff | 0.2 | −2.4 | 2.1 | 0.0 | −0.6 | 0.8 |
| Prob | 0.563 | 0.009 | 0.042 | — | 0.754 | 0.606 |

| Stat | ERTLPN % NOT ABS | LRTLPN % NOT ABS |
|---|---|---|
| Mean1 | 83.6 | 86.5 |
| Mean2 | 81.0 | 82.9 |
| Locs | 12 | 13 |
| Reps | 14 | 16 |
| Diff | 2.6 | 3.6 |
| Prob | 0.699 | 0.618 |

TABLE 5C

INBREDS IN HYBRID COMBINATION REPORT
Variety #1: HYBRID CONTAINING PH8JR
Variety #2: 36N70

| Stat | YIELD BU/A 56# ABS | YIELD BU/A 56# % MN | MST PCT % MN | EGRWTH SCORE % MN | ESTCNT COUNT % MN | GDUSHD GDU % MN |
|---|---|---|---|---|---|---|
| Mean1 | 178.7 | 101.2 | 96.3 | 90.6 | 102.8 | 101.7 |
| Mean2 | 173.6 | 98.4 | 94.4 | 98.8 | 104.0 | 97.7 |
| Locs | 295 | 295 | 296 | 17 | 5 | 27 |
| Reps | 306 | 306 | 307 | 19 | 7 | 31 |

TABLE 5C-continued

INBREDS IN HYBRID COMBINATION REPORT
Variety #1: HYBRID CONTAINING PH8JR
Variety #2: 36N70

| Stat | | | | | | |
|---|---|---|---|---|---|---|
| Diff | 5.1 | 2.8 | -1.9 | -8.2 | -1.2 | 4.0 |
| Prob | 0.000 | 0.000 | 0.001 | 0.060 | 0.804 | 0.000 |

| Stat | GDUSLK GDU % MN | STKCNT COUNT % MN | PLTHT CM % MN | EARHT CM % MN | STAGRN SCORE % MN | STKLDG % NOT % MN |
|---|---|---|---|---|---|---|
| Mean1 | 101.8 | 99.5 | 103.6 | 107.2 | 101.2 | 101.3 |
| Mean2 | 97.8 | 100.2 | 96.0 | 102.1 | 101.2 | 97.0 |
| Locs | 23 | 196 | 27 | 27 | 41 | 1 |
| Reps | 27 | 295 | 34 | 34 | 46 | 2 |
| Diff | 4.0 | -0.7 | 7.7 | 5.1 | -0.1 | 4.2 |
| Prob | 0.000 | 0.080 | 0.000 | 0.000 | 0.990 | — |

| Stat | ABTSTK % NOT % MN | DRPEAR % NOT % MN | TSTWT LB/BU ABS | GLFSPT SCORE ABS | NLFBLT SCORE ABS | GOSWLT SCORE ABS |
|---|---|---|---|---|---|---|
| Mean1 | 68.7 | 99.7 | 55.5 | 4.0 | 5.3 | 8.0 |
| Mean2 | 86.0 | 102.0 | 56.4 | 4.5 | 7.1 | 8.0 |
| Locs | 3 | 2 | 233 | 3 | 11 | 1 |
| Reps | 18 | 2 | 237 | 5 | 17 | 2 |
| Diff | -17.3 | -2.3 | -0.9 | -0.5 | -1.8 | 0.0 |
| Prob | 0.227 | 0.233 | 0.000 | 0.225 | 0.001 | — |

| Stat | ANTROT SCORE ABS | FUSERS SCORE ABS | GIBERS SCORE ABS | EYESPT SCORE ABS | ECBDPE % NOT ABS | ECB1LF SCORE ABS |
|---|---|---|---|---|---|---|
| Mean1 | 4.5 | 5.1 | 7.3 | 4.0 | 97.5 | 3.3 |
| Mean2 | 4.8 | 5.9 | 6.5 | 5.5 | 97.3 | 3.7 |
| Locs | 4 | 7 | 4 | 1 | 10 | 1 |
| Reps | 8 | 11 | 6 | 2 | 12 | 3 |
| Diff | -0.3 | -0.9 | 0.8 | -1.5 | 0.2 | -0.3 |
| Prob | 0.804 | 0.143 | 0.488 | — | 0.871 | — |

| Stat | ECB2SC SCORE ABS | HSKCVR SCORE ABS | GIBROT SCORE ABS | DIPROT SCORE ABS | BRTSTK % NOT ABS | HD SMT % NOT ABS |
|---|---|---|---|---|---|---|
| Mean1 | 4.5 | 4.0 | 4.8 | 3.5 | 95.9 | 99.5 |
| Mean2 | 4.6 | 5.5 | 4.4 | 6.5 | 95.9 | 99.3 |
| Locs | 7 | 4 | 8 | 1 | 8 | 6 |
| Reps | 11 | 5 | 15 | 2 | 10 | 8 |
| Diff | -0.1 | -1.5 | 0.3 | -3.0 | 0.0 | 0.2 |
| Prob | 0.801 | 0.058 | 0.756 | — | 0.997 | 0.777 |

| Stat | ERTLPN % NOT ABS | LRTLPN % NOT ABS |
|---|---|---|
| Mean1 | 80.7 | 88.6 |
| Mean2 | 70.4 | 89.0 |
| Locs | 16 | 11 |
| Reps | 18 | 14 |
| Diff | 10.3 | -0.4 |
| Prob | 0.092 | 0.946 |

All publications, patents and patent applications mentioned in the specification are indicative of the level of those skilled in the art to which this invention pertains. All such publications, patents and patent applications are incorporated by reference herein for the purpose cited to the same extent as if each was specifically and individually indicated to be incorporated by reference herein.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

What is claimed is:

1. A seed comprising at least one set of the chromosomes of maize inbred line PH8JR, representative seed of said line having been deposited under ATCC Accession No. PTA-6357, wherein said chromosomes comprise all of the alleles of inbred line PH8JR at the SSR loci listed in Table 2.

2. A maize plant produced by growing the seed of claim 1.

3. A maize plant part of the maize plant of claim 2.

4. The seed of claim 1, wherein said seed is an F1 hybrid maize seed produced by crossing a plant of maize inbred line PH8JR with a different maize plant and harvesting the resultant F1 hybrid maize seed.

5. A maize plant produced by growing the F1 hybrid maize seed of claim 4.

6. A maize plant part of the maize plant of claim 5.

7. An F1 hybrid maize seed comprising an inbred corn plant cell of inbred maize line PH8JR, representative seed of said line having been deposited under ATCC Accession No. PTA-6357.

8. A maize plant produced by growing the F1 hybrid maize seed of claim 7.

9. The F1 hybrid maize seed of claim 7 wherein the inbred corn plant cell comprises two sets of chromosomes of maize inbred line PH8JR, wherein said chromosomes comprise all of the alleles of inbred line PH8JR at the SSR loci listed in Table 2.

10. A maize plant produced by growing the F1 hybrid maize seed of claim 9.

11. A maize plant having all the physiological and morphological characteristics of inbred line PH8JR, wherein a sample of the seed of inbred line PH8JR was deposited under ATCC Accession Number PTA-6357.

12. A process of producing maize seed, comprising crossing a first parent maize plant with a second parent maize plant, wherein one or both of the first or the second parent maize plants is the plant of claim 11, wherein seed is allowed to form.

13. The maize seed produced by the process of claim 12.

14. The maize seed of claim 13, wherein the maize seed is hybrid seed.

15. A hybrid maize plant, or its parts, produced by growing said hybrid seed of claim 14.

16. A maize seed produced by growing said maize plant of claim 15 and harvesting the resultant maize seed.

17. The maize plant of claim 11, further comprising an SSR profile in accordance with the profile shown in Table 2.

18. A cell of the maize plant of claim 11.

19. The cell of claim 18, wherein said cell is further defined as having an SSR profile in accordance with the profile shown in Table 2.

20. A seed comprising the cell of claim 18.

21. A method of producing a maize plant derived from the maize plant of claim 11, the method comprising the steps of:
    (a) growing a progeny plant produced by crossing the plant of claim 11 with a second maize plant;
    (b) crossing the progeny plant with itself or a different plant to produce a seed of a progeny plant of a subsequent generation;
    (c) growing a progeny plant of a subsequent generation from said seed and crossing the progeny plant of a subsequent generation with itself or a different plant; and
    (d) repeating steps (b) and (c) for an additional 0-5 generations to produce a maize plant derived from the maize plant of claim 11.

22. The method of claim 21 wherein the maize plant derived from the maize plant of claim 11 is an inbred maize plant.

23. The method of claim 22, further comprising the step of crossing the inbred maize plant derived from the maize plant of claim 11 with a second, distinct inbred maize plant to produce an F1 hybrid maize plant.

24. A method for developing a maize plant in a maize plant breeding program using plant breeding techniques comprising employing a maize plant, or its parts, as a source of plant breeding material comprising using the maize plant of claim 11, or parts thereof, as a source of said breeding material.

25. The method for developing a maize plant in a maize plant breeding program of claim 24 wherein plant breeding techniques are selected from the group consisting of recurrent selection, backcrossing, pedigree breeding, restriction fragment length polymorphism enhanced selection, genetic marker enhanced selection, and transformation.

26. The method of claim 25 wherein the plant breeding technique comprises the steps of:
    (a) obtaining the molecular marker profile of the maize plant of claim 11;
    (b) obtaining an F1 hybrid seed for which the maize plant of claim 11 is a parent;
    (c) crossing a plant grown from the F1 hybrid seed with a different maize plant; and
    (d) selecting progeny that retain the molecular marker profile of PH8JR.

27. A process of producing a conversion of maize inbred variety PH8JR comprising at least one new trait, the process comprising:
    (a) crossing a plant of maize inbred variety PH8JR, representative seed of which has been deposited under ATCC Accession Number PTA-6357, with a plant of another maize variety that comprises at least one new trait to produce progeny seed;
    (b) harvesting and planting the progeny seed to produce at least one progeny plant of a subsequent generation, said progeny plant comprising the at least one new trait;
    (c) crossing the progeny plant with a plant of maize inbred variety PH8JR to produce backcross progeny seed;
    (d) harvesting and planting the backcross progeny seed to produce at least one backcross progeny plant; and
    (e) repeating steps (c) and (d) for at least three additional generations to produce a converted plant of inbred variety PH8JR, wherein the converted plant of inbred variety PH8JR comprises the at least one new trait.

28. A converted plant of inbred variety PH8JR produced by the process of claim 27.

29. The maize plant of claim 28, wherein the at least one new trait is selected from the group consisting of herbicide tolerance; insect resistance; resistance to bacterial, fungal, nematode or viral disease; yield enhancement; waxy starch; improved nutritional quality; male sterility and restoration of male fertility.

30. The maize plant of claim 28, wherein the at least one new trait is male sterility.

31. A plant of inbred maize variety PH8JR produced by the method of claim 25, wherein the plant breeding technique is transformation.

32. The maize plant of claim 31, wherein said plant is further defined as comprising a transgene conferring a trait selected from the group consisting of male sterility, herbicide resistance, insect resistance, and disease resistance.

\* \* \* \* \*